(12) United States Patent
Hassan et al.

(10) Patent No.: US 8,658,423 B2
(45) Date of Patent: *Feb. 25, 2014

(54) INSULIN-LIKE GROWTH FACTOR II (IGF-II) BINDING FACTORS

(75) Inventors: Andrew Bassim Hassan, Bristol (GB); Oliver Zaccheo, Bristol (GB); Stuart Prince, Bristol (GB)

(73) Assignee: Cancer Research Technology Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/618,064

(22) Filed: Sep. 14, 2012

(65) Prior Publication Data

US 2013/0071366 A1    Mar. 21, 2013

Related U.S. Application Data

(63) Continuation of application No. 11/990,479, filed as application No. PCT/GB2006/003011 on Aug. 11, 2006, now Pat. No. 8,293,875.

(30) Foreign Application Priority Data

Aug. 15, 2005 (GB) .................................. 0516722.6

(51) Int. Cl.
*C12N 5/00* (2006.01)
*C12N 15/63* (2006.01)
*C07K 14/61* (2006.01)
*C07K 14/575* (2006.01)

(52) U.S. Cl.
USPC ......... 435/325; 435/320.1; 530/303; 530/399

(58) Field of Classification Search
None
See application file for complete search history.

(56) References Cited

U.S. PATENT DOCUMENTS 8,293,875 B2    10/2012    Hassan et al.

FOREIGN PATENT DOCUMENTS

| JP | 07-053401 A1 | 2/1995 |
| WO | WO 2004/007543 A1 | 1/2004 |
| WO | WO 2007/020402 A1 | 2/2007 |

OTHER PUBLICATIONS

Waters et al., Curr. Issues Mol. Biol., vol. 3(3) 57-65, 2001.*
Zhukov et al., Protein Science, vol. 9, 273-279, 2001.*
[No Author Listed] UniProt Accession No. Q95LC7; Killian et al.; Dec. 1, 2001. 3 pages.
[No Author Listed] UniProt Accession No. Q9N1T0; Killian et al.; Oct. 1, 2000. 3 pages.
Bassim Hassan, Keys to the hidden treasures of the mannose 6-phosphate/insulin-like growth factor 2 receptor. Am J Pathol. Jan. 2003;162(1):3-6.
Breuhahn et al., Molecular profiling of human hepatocellular carcinoma defines mutually exclusive interferon regulation and insulin-like growth factor II overexpression. Cancer Res. Sep. 1, 2004;64(17):6058-64.
Brown et al., Structure of a functional IGF2R fragment determined from the anomalous scattering of sulfur. EMBO J. Mar. 1, 2002;21(5):1054-62.
Burns et al., Cell survival and proliferation are modified by insulin-like growth factor 2 between days 9 and 10 of mouse gestation. Development. Oct. 2001;128(19):3819-30.
Byrd et al., Disruption of ligand binding to the insulin-like growth factor II/mannose 6-phosphate receptor by cancer-associated missense mutations. J Biol Chem. Aug. 20, 1999;274(34):24408-16.
Clairmont et al., Chicken and Xenopus mannose 6-phosphate receptors fail to bind insulin-like growth factor II. J Biol Chem. Oct. 5, 1989;264(28):16390-2.
Dahms et al., The bovine mannose 6-phosphate/insulin-like growth factor II receptor. The role of arginine residues in mannose 6-phosphate binding. J Biol Chem. Mar. 15, 1993;268(8):5457-63.
Dennis et al., Cellular activation of latent transforming growth factor beta requires binding to the cation-independent mannose 6-phosphate/insulin-like growth factor type II receptor. Proc Natl Acad. Sci U S A. Jan. 15, 1991; 88(2):580-4.
Devi et al., An insulin-like growth factor II (IGF-II) affinity-enhancing domain localized within extracytoplasmic repeat 13 of the IGF-II/mannose 6-phosphate receptor. Mol Endocrinol. Nov. 1998;12(11):1661-72.
Devi et al., Altered ligand binding by insulin-like growth factor II/mannose 6-phosphate receptors bearing missense mutations in human cancers. Cancer Res. Sep. 1, 1999;59(17):4314-9.
El-Badry et al., Insulin-like growth factor II acts as an autocrine growth and motility factor in human rhabdomyosarcoma tumors. Cell Growth Differ. Jul. 1990;1(7):325-31.
Garmroudi et al., Truncated forms of the insulin-like growth factor II (IGF-II)/mannose 6-phosphate receptor encompassing the IGF-II binding site: characterization of a point mutation that abolishes IGF-II binding. Mol Endocrinol. Jun. 1996;10(6):642-51.
Grimme et al., Endocytosis of insulin-like growth factor II by a mini-receptor based on repeat 11 of the mannose 6-phosphate/insulin-like growth factor II receptor. J Biol Chem. Oct. 27, 2000;275(43):33697-703.
Halperin et al., Protein-protein interactions; coupling of structurally conserved residues and of hot spots across interfaces. Implications for docking. Structure. Jun. 2004;12(6):1027-38.
Hancock et al., Identification of residues essential for carbohydrate recognition by the insulin-like growth factor II/mannose 6-phosphate receptor. J Biol Chem. Mar. 29, 2002;277(13):11255-64. Epub Jan. 17, 2002.

(Continued)

*Primary Examiner* — Marianne P Allen
(74) *Attorney, Agent, or Firm* — Wolf, Greenfield & Sacks, P.C.

(57) ABSTRACT

This invention relates to modified IGF-II binding domains of the Insulin-like Growth Factor 2 Receptor (IGF2R) which have enhanced binding affinity for IGF-II relative to the wild type IGF-II binding domain. Suitable IGF-II binding domains may be modified, for example, by substituting residue E1544 for a non-acidic residue. These modified domains may be useful in the sequestration of Insulin-like Growth Factor II (IGF-II), for example, in the treatment of cancer.

19 Claims, 12 Drawing Sheets

(56) References Cited

OTHER PUBLICATIONS

Harper et al., Soluble IGF2 Receptor Rescues Apc$^{Min/+}$ Intestinal Adenoma Progression Induced by IGF2 Loss of Imprinting. Cancer Res 2006; 66(4): 1940-8.

Hobba et al., The insulin-like growth factor (IGF) binding site of bovine insulin-like growth factor binding protein-2 (bIGFBP-2) probed by iodination. J Biol Chem. Nov. 29, 1996;271(48):30529-36.

Jamieson et al., M6P/IGF2R loss of heterozygosity in head and neck cancer associated with poor patient prognosis. BMC Cancer. Feb. 13, 2003;3:4. Epub Feb. 13, 2003.

Killian et al., Marsupials and Eutherians reunited: genetic evidence for the Theria hypothesis of mammalian evolution. Mamm Genome. Jul. 2001;12(7):513-7.

Killian et al., M6P/IGF2R imprinting evolution in mammals. Mol Cell. Apr. 2000;5(4):707-16.

Kim et al., IGF-II-mediated COX-2 gene expression in human keratinocytes through extracellular signal-regulated kinase pathway. J Invest Dermatol. Sep. 2004;123(3):547-55.

Kong et al., M6P/IGF2R is mutated in squamous cell carcinoma of the lung. Oncogene. Mar. 16, 2000;19(12):1572-8.

Kreiling et al., Domain interactions of the mannose 6-phosphate/insulin-like growth factor II receptor. J Biol Chem. Jun. 3, 2005;280(22):21067-77. Epub Mar. 30, 2005.

Lau et al., Loss of the imprinted IGF2/cation-independent mannose 6-phosphate receptor results in fetal overgrowth and perinatal lethality. Genes Dev. Dec. 15, 1994;8(24):2953-63.

Lee et al., Increased Expression of the Mannose 6-Phosphate/Insulin-Like Growth Factor-II Receptor in Breast Cancer Cells Alters Tumorigenic Properties In Vitro and In Vivo. Int. J. Cancer. 2003;107:564-70.

Li et al., Demonstration of tumor suppression by mannose 6-phosphate/insulin-like growth factor 2 receptor. Oncogene. Dec. 16, 2004;23(58):9359-68.

Li et al., Magnitude of the hydrophobic effect at central versus peripheral sites in protein-protein interfaces. Structure. Feb. 2005;13(2):297-307.

Linnell et al., Real time kinetics of insulin-like growth factor II (IGF-II) interaction with the IGF-II/mannose 6-phosphate receptor: the effects of domain 13 and pH. J Biol Chem. Jun. 29, 2001;276(26):23986-91. Epub Apr. 10, 2001.

Lobel et al., Cloning and sequence analysis of the cation-independent mannose 6-phosphate receptor. J Biol Chem. Feb. 15, 1988;263(5):2563-70.

Ludwig et al., Mouse mutants lacking the type 2 IGF receptor (IGF2R) are rescued from perinatal lethality in Igf2 and Igf1r null backgrounds. Dev Biol. Aug. 1, 1996;177(2):517-35.

Matsunaka et al., Ligand-Specific Antibodies to Insulin-Like Growth Factors Suppress Intestinal Polyp Formation in Apc$^{+/-}$ Mice. Mol Cancer Ther 2010; 9:419-28.

Nosho et al., Interplay of insulin-like growth factor-II, insulin-like growth factor-I, insulin-like growth factor-I receptor, COX-2, and matrix metalloproteinase-7, play key roles in the early stage of colorectal carcinogenesis. Clin Cancer Res. Dec. 1, 2004;10(23):7950-7.

O'Gorman et al., Insulin-like growth factor-II/mannose 6-phosphate receptor overexpression reduces growth of choriocarcinoma cells in vitro and in vivo. Endocrinology. Nov. 2002;143(11):4287-94.

Oka et al., Direct demonstration of rapid insulin-like growth factor II Receptor internalization and recycling in rat adipocytes. Insulin stimulates $^{125}$I-insulin-like growth factor II degradation by modulating the IGF-II receptor recycling process. J Biol Chem. Aug. 5, 1985;260(16):9435-42.

Olson et al., Structural basis for recognition of phosphorylated high mannose oligosaccharides by the cation-dependent mannose 6-phosphate receptor. J Biol Chem. Oct. 15, 1999;274(42):29889-96.

Olson et al., Structure of uPAR, plasminogen, and sugar-binding sites of the 300 kDa mannose 6-phosphate receptor. EMBO J. May 19, 2004;23(10):2019-28. Epub Apr. 15, 2004.

Oshima et al., The human cation-independent mannose 6-phosphate receptor. Cloning and sequence of the full-length cDNA and expression of functional receptor in COS cells. J Biol Chem. Feb. 15, 1988;263(5):2553-62.

Rajamani et al., Anchor residues in protein-protein interactions. Proc Natl Acad Sci U S A. Aug. 3, 2004;101(31):11287-92. Epub Jul. 21, 2004.

Ravenel et al., Loss of imprinting of insulin-like growth factor-II (IGF2) gene in distinguishing specific biologic subtypes of Wilms tumor. J Natl Cancer Inst. Nov. 21, 2001;93(22):1698-703.

Reddy et al., Identification of a low affinity mannose 6-phosphate-binding site in domain 5 of the cation-independent mannose 6-phosphate receptor. J Biol Chem. Sep. 10, 2004;279(37):38658-67. Epub Jul. 12, 2004.

Roberts et al., Molecular basis of lysosomal enzyme recognition: three-dimensional structure of the cation-dependent mannose 6-phosphate receptor. Cell. May 15, 1998;93(4):639-48.

Roche et al., Computational model for the IGF-II/IGF2r complex that is predictive of mutational and surface plasmon resonance data. Proteins. Aug. 15, 2006;64(3):758-68.

Sakano et al., The design, expression, and characterization of human insulin-like growth factor II (IGF-II) mutants specific for either the IGF-II/cation-independent mannose 6-phosphate receptor or IGF-I receptor. J Biol Chem. Nov. 5, 1991;266(31):20626-35.

Schmidt et al., Localization of the insulin-like growth factor II binding site to amino acids 1508-1566 in repeat 11 of the mannose 6-phosphate/insulin-like growth factor II receptor. J Biol Chem. Jun. 23, 1995;270(25):14975-82.

Scott et al., Soluble insulin-like growth factor-II/mannose 6-P receptor inhibits deoxyribonucleic acid synthesis in cultured rat hepatocytes. Endocrinology. Mar. 1996;137(3):873-8.

Souza et al., Expression of the wild-type insulin-like growth factor II receptor gene suppresses growth and causes death in colorectal carcinoma cells. Oncogene. Jul. 15, 1999;18(28):4063-8.

Terasawa et al., Solution structure of human insulin-like growth factor II; recognition sites for receptors and binding proteins. EMBO J. Dec. 1, 1994;13(23):5590-7.

Tong et al., The cation-independent mannose 6-phosphate receptor binds insulin-like growth factor II. J Biol Chem. Feb. 25, 1988;263(6):2585-8.

Usón et al., Locating the anomalous scatterer substructures in halide and sulfur phasing. Acta Crystallogr D Biol Crystallogr. Jan. 2003;59(Pt 1):57-66. Epub Dec. 19, 2002.

Wu et al., Multimerization of a chimeric anti-CD20 single-chain Fv-Fc fusion protein is mediated through variable domain exchange. Protein Eng. Dec. 2001;14(12):1025-33.

Zaccheo et al., Kinetics of insulin-like growth factor II (IGF-II) interaction with domain 11 of the human IGF-II/mannose 6-phosphate receptor: function of CD and AB loop solvent-exposed residues. J Mol Biol. Jun. 2, 2006;359(2):403-21. Epub Apr. 6, 2006.

* cited by examiner

AB loop            CD loop

1311-NEHDDCQVTRPSTGHLFGLSSLSGRAGFTAAYERSQLVYKSICSENEMCFSYGAGFGQTRIYVGRANRE

FG loop

LRIYDQVLQLVYKESSPCFSKEGLSYKSVISFYCRFRAGPTNRPKLISLDRQTCTLFFSNRTFLACEQAT-1650

Figure 2A

YSESCLVTNSTCSENEMCFGVGACFGQTRIGVCRANRELRYVDQVLQLVYKDSPCPSKSGLSYKSVISPYCRFEAG
Y1542A  A-----------------------------------------------------------------------
S1543A  -A----------------------------------------------------------------------
R1544K  --R---------------------------------------------------------------------
R1546V  ---V--------------------------------------------------------------------
R1546K  ---K--------------------------------------------------------------------
R1565A  ----A-------------------------------------------------------------------
F1567A  ---------------A--------------------------------------------------------
Q1568A  ----------------A-------------------------------------------------------
T1570A  ------------------A-----------------------------------------------------
I1572A  --------------------A---------------------------------------------------
I1572T  --------------------T---------------------------------------------------
S1596A  -----------------------------------------A------------------------------
Q1615R  ------------------------------------------------------------------------R

Figure 2B

SEQUENCE LISTING

<160> NUMBER OF SEQ ID NOS: 41

<210> SEQ ID NO 1
<211> LENGTH: 2491
<212> TYPE: PRT
<213> ORGANISM: H. sapiens

<400> SEQUENCE: 1

Met Gly Ala Ala Ala Gly Arg Ser Pro His Leu Gly Pro Ala Pro Ala
1               5                   10                  15

Arg Arg Pro Gln Arg Ser Leu Leu Leu Leu Gln Leu Leu Leu Leu Val
                20                  25                  30

Ala Ala Pro Gly Ser Thr Gln Ala Gln Ala Ala Pro Phe Pro Glu Leu
            35                  40                  45

```
Cys Ser Tyr Thr Trp Glu Ala Val Asp Thr Lys Asn Asn Val Leu Tyr
     50                  55                  60

Lys Ile Asn Ile Cys Gly Ser Val Asp Ile Val Gln Cys Gly Pro Ser
 65                  70                  75                  80

Ser Ala Val Cys Met His Asp Leu Lys Thr Arg Thr Tyr His Ser Val
                 85                  90                  95

Gly Asp Ser Val Leu Arg Ser Ala Thr Arg Ser Leu Leu Glu Phe Asn
            100                 105                 110

Thr Thr Val Ser Cys Asp Gln Gln Gly Thr Asn His Arg Val Gln Ser
            115                 120                 125

Ser Ile Ala Phe Leu Cys Gly Lys Thr Leu Gly Thr Pro Glu Phe Val
    130                 135                 140

Thr Ala Thr Glu Cys Val His Tyr Phe Glu Trp Arg Thr Thr Ala Ala
145                 150                 155                 160

Cys Lys Lys Asp Ile Phe Lys Ala Asn Lys Glu Val Pro Cys Tyr Val
                165                 170                 175

Phe Asp Glu Glu Leu Arg Lys His Asp Leu Asn Pro Leu Ile Lys Leu
            180                 185                 190

Ser Gly Ala Tyr Leu Val Asp Asp Ser Asp Pro Asp Thr Ser Leu Phe
    195                 200                 205

Ile Asn Val Cys Arg Asp Ile Asp Thr Leu Arg Asp Pro Gly Ser Gln
210                 215                 220

Leu Arg Ala Cys Pro Pro Gly Thr Ala Ala Cys Leu Val Arg Gly His
225                 230                 235                 240

Gln Ala Phe Asp Val Gly Gln Pro Arg Asp Gly Leu Lys Leu Val Arg
                245                 250                 255

Lys Asp Arg Leu Val Leu Ser Tyr Val Arg Glu Glu Ala Gly Lys Leu
            260                 265                 270

Asp Phe Cys Asp Gly His Ser Pro Ala Val Thr Ile Thr Phe Val Cys
        275                 280                 285

Pro Ser Glu Arg Arg Glu Gly Thr Ile Pro Lys Leu Thr Ala Lys Ser
    290                 295                 300

Asn Cys Arg Tyr Glu Ile Glu Trp Ile Thr Glu Tyr Ala Cys His Arg
305                 310                 315                 320

Asp Tyr Leu Glu Ser Lys Thr Cys Ser Leu Ser Gly Glu Gln Gln Asp
                325                 330                 335

Val Ser Ile Asp Leu Thr Pro Leu Ala Gln Ser Gly Gly Ser Ser Tyr
            340                 345                 350

Ile Ser Asp Gly Lys Glu Tyr Leu Phe Tyr Leu Asn Val Cys Gly Glu
        355                 360                 365

Thr Glu Ile Gln Phe Cys Asn Lys Lys Gln Ala Ala Val Cys Gln Val
    370                 375                 380

Lys Lys Ser Asp Thr Ser Gln Val Lys Ala Ala Gly Arg Tyr His Asn
385                 390                 395                 400

Gln Thr Leu Arg Tyr Ser Asp Gly Asp Leu Thr Leu Ile Tyr Phe Gly
                405                 410                 415

Gly Asp Glu Cys Ser Ser Gly Phe Gln Arg Met Ser Val Ile Asn Phe
            420                 425                 430

Glu Cys Asn Lys Thr Ala Gly Asn Asp Gly Lys Gly Thr Pro Val Phe
        435                 440                 445

Thr Gly Glu Val Asp Cys Thr Tyr Phe Phe Trp Asp Thr Glu Tyr
    450                 455                 460

Ala Cys Val Lys Glu Lys Glu Asp Leu Leu Cys Gly Ala Thr Asp Gly
465                 470                 475                 480
```

```
Lys Lys Arg Tyr Asp Leu Ser Ala Leu Val Arg His Ala Glu Pro Glu
            485                 490                 495
Gln Asn Trp Glu Ala Val Asp Gly Ser Gln Thr Glu Thr Glu Lys Lys
            500                 505                 510
His Phe Phe Ile Asn Ile Cys His Arg Val Leu Gln Glu Gly Lys Ala
            515                 520                 525
Arg Gly Cys Pro Glu Asp Ala Ala Val Cys Ala Val Asp Lys Asn Gly
            530                 535                 540
Ser Lys Asn Leu Gly Lys Phe Ile Ser Pro Met Lys Glu Lys Gly
545                 550                 555                 560
Asn Ile Gln Leu Ser Tyr Ser Asp Gly Asp Cys Gly His Gly Lys
            565                 570                 575
Lys Ile Lys Thr Asn Ile Thr Leu Val Cys Lys Pro Gly Asp Leu Glu
            580                 585                 590
Ser Ala Pro Val Leu Arg Thr Ser Gly Glu Gly Gly Cys Phe Tyr Glu
            595                 600                 605
Phe Glu Trp Arg Thr Ala Ala Ala Cys Val Leu Ser Lys Thr Glu Gly
            610                 615                 620
Glu Asn Cys Thr Val Phe Asp Ser Gln Ala Gly Phe Ser Phe Asp Leu
625                 630                 635                 640
Ser Pro Leu Thr Lys Lys Asn Gly Ala Tyr Lys Val Glu Thr Lys Lys
            645                 650                 655
Tyr Asp Phe Tyr Ile Asn Val Cys Gly Pro Val Ser Val Ser Pro Cys
            660                 665                 670
Gln Pro Asp Ser Gly Ala Cys Gln Val Ala Lys Ser Asp Glu Lys Thr
            675                 680                 685
Trp Asn Leu Gly Leu Ser Asn Ala Lys Leu Ser Tyr Tyr Asp Gly Met
            690                 695                 700
Ile Gln Leu Asn Tyr Arg Gly Gly Thr Pro Tyr Asn Asn Glu Arg His
705                 710                 715                 720
Thr Pro Arg Ala Thr Leu Ile Thr Phe Leu Cys Asp Arg Asp Ala Gly
            725                 730                 735
Val Gly Phe Pro Glu Tyr Gln Glu Glu Asp Asn Ser Thr Tyr Asn Phe
            740                 745                 750
Arg Trp Tyr Thr Ser Tyr Ala Cys Pro Glu Glu Pro Leu Glu Cys Val
            755                 760                 765
Val Thr Asp Pro Ser Thr Leu Glu Gln Tyr Asp Leu Ser Ser Leu Ala
            770                 775                 780
Lys Ser Glu Gly Gly Leu Gly Gly Asn Trp Tyr Ala Met Asp Asn Ser
785                 790                 795                 800
Gly Glu His Val Thr Trp Arg Lys Tyr Tyr Ile Asn Val Cys Arg Pro
            805                 810                 815
Leu Asn Pro Val Pro Gly Cys Asn Arg Tyr Ala Ser Ala Cys Gln Met
            820                 825                 830
Lys Tyr Glu Lys Asp Gln Gly Ser Phe Thr Glu Val Val Ser Ile Ser
            835                 840                 845
Asn Leu Gly Met Ala Lys Thr Gly Pro Val Val Glu Asp Ser Gly Ser
            850                 855                 860
Leu Leu Leu Glu Tyr Val Asn Gly Ser Ala Cys Thr Thr Ser Asp Gly
865                 870                 875                 880
Arg Gln Thr Thr Tyr Thr Thr Arg Ile His Leu Val Cys Ser Arg Gly
            885                 890                 895
```

```
Arg Leu Asn Ser His Pro Ile Phe Ser Leu Asn Trp Glu Cys Val Val
            900                 905                 910

Ser Phe Leu Trp Asn Thr Glu Ala Ala Cys Pro Ile Gln Thr Thr Thr
            915                 920                 925

Asp Thr Asp Gln Ala Cys Ser Ile Arg Asp Pro Asn Ser Gly Phe Val
            930                 935                 940

Phe Asn Leu Asn Pro Leu Asn Ser Ser Gln Gly Tyr Asn Val Ser Gly
945                 950                 955                 960

Ile Gly Lys Ile Phe Met Phe Asn Val Cys Gly Thr Met Pro Val Cys
            965                 970                 975

Gly Thr Ile Leu Gly Lys Pro Ala Ser Gly Cys Glu Ala Glu Thr Gln
            980                 985                 990

Thr Glu Glu Leu Lys Asn Trp Lys Pro Ala Arg Pro Val Gly Ile Glu
            995                 1000                1005

Lys Ser Leu Gln Leu Ser Thr Glu Gly Phe Ile Thr Leu Thr Tyr
            1010                1015                1020

Lys Gly Pro Leu Ser Ala Lys Gly Thr Ala Asp Ala Phe Ile Val
            1025                1030                1035

Arg Phe Val Cys Asn Asp Asp Val Tyr Ser Gly Pro Leu Lys Phe
            1040                1045                1050

Leu His Gln Asp Ile Asp Ser Gly Gln Gly Ile Arg Asn Thr Tyr
            1055                1060                1065

Phe Glu Phe Glu Thr Ala Leu Ala Cys Val Pro Ser Pro Val Asp
            1070                1075                1080

Cys Gln Val Thr Asp Leu Ala Gly Asn Glu Tyr Asp Leu Thr Gly
            1085                1090                1095

Leu Ser Thr Val Arg Lys Pro Trp Thr Ala Val Asp Thr Ser Val
            1100                1105                1110

Asp Gly Arg Lys Arg Thr Phe Tyr Leu Ser Val Cys Asn Pro Leu
            1115                1120                1125

Pro Tyr Ile Pro Gly Cys Gln Gly Ser Ala Val Gly Ser Cys Leu
            1130                1135                1140

Val Ser Glu Gly Asn Ser Trp Asn Leu Gly Val Val Gln Met Ser
            1145                1150                1155

Pro Gln Ala Ala Ala Asn Gly Ser Leu Ser Ile Met Tyr Val Asn
            1160                1165                1170

Gly Asp Lys Cys Gly Asn Gln Arg Phe Ser Thr Arg Ile Thr Phe
            1175                1180                1185

Glu Cys Ala Gln Ile Ser Gly Ser Pro Ala Phe Gln Leu Gln Asp
            1190                1195                1200

Gly Cys Glu Tyr Val Phe Ile Trp Arg Thr Val Glu Ala Cys Pro
            1205                1210                1215

Val Val Arg Val Glu Gly Asp Asn Cys Glu Val Lys Asp Pro Arg
            1220                1225                1230

His Gly Asn Leu Tyr Asp Leu Lys Pro Leu Gly Leu Asn Asp Thr
            1235                1240                1245

Ile Val Ser Ala Gly Glu Tyr Thr Tyr Tyr Phe Arg Val Cys Gly
            1250                1255                1260

Lys Leu Ser Ser Asp Val Cys Pro Thr Ser Asp Lys Ser Lys Val
            1265                1270                1275

Val Ser Ser Cys Gln Glu Lys Arg Glu Pro Gln Gly Phe His Lys
            1280                1285                1290

Val Ala Gly Leu Leu Thr Gln Lys Leu Thr Tyr Glu Asn Gly Leu
            1295                1300                1305
```

-continued

```
Leu Lys Met Asn Phe Thr Gly Gly Asp Thr Cys His Lys Val Tyr
    1310            1315             1320

Gln Arg Ser Thr Ala Ile Phe Phe Tyr Cys Asp Arg Gly Thr Gln
    1325            1330             1335

Arg Pro Val Phe Leu Lys Glu Thr Ser Asp Cys Ser Tyr Leu Phe
    1340            1345             1350

Glu Trp Arg Thr Gln Tyr Ala Cys Pro Pro Phe Asp Leu Thr Glu
    1355            1360             1365

Cys Ser Phe Lys Asp Gly Ala Gly Asn Ser Phe Asp Leu Ser Ser
    1370            1375             1380

Leu Ser Arg Tyr Ser Asp Asn Trp Glu Ala Ile Thr Gly Thr Gly
    1385            1390             1395

Asp Pro Glu His Tyr Leu Ile Asn Val Cys Lys Ser Leu Ala Pro
    1400            1405             1410

Gln Ala Gly Thr Glu Pro Cys Pro Pro Glu Ala Ala Ala Cys Leu
    1415            1420             1425

Leu Gly Gly Ser Lys Pro Val Asn Leu Gly Arg Val Arg Asp Gly
    1430            1435             1440

Pro Gln Trp Arg Asp Gly Ile Ile Val Leu Lys Tyr Val Asp Gly
    1445            1450             1455

Asp Leu Cys Pro Asp Gly Ile Arg Lys Lys Ser Thr Thr Ile Arg
    1460            1465             1470

Phe Thr Cys Ser Glu Ser Gln Val Asn Ser Arg Pro Met Phe Ile
    1475            1480             1485

Ser Ala Val Glu Asp Cys Glu Tyr Thr Phe Ala Trp Pro Thr Ala
    1490            1495             1500

Thr Ala Cys Pro Met Lys Ser Asn Glu His Asp Asp Cys Gln Val
    1505            1510             1515

Thr Asn Pro Ser Thr Gly His Leu Phe Asp Leu Ser Ser Leu Ser
    1520            1525             1530

Gly Arg Ala Gly Phe Thr Ala Ala Tyr Ser Glu Lys Gly Leu Val
    1535            1540             1545

Tyr Met Ser Ile Cys Gly Glu Asn Glu Asn Cys Pro Pro Gly Val
    1550            1555             1560

Gly Ala Cys Phe Gly Gln Thr Arg Ile Ser Val Gly Lys Ala Asn
    1565            1570             1575

Lys Arg Leu Arg Tyr Val Asp Gln Val Leu Gln Leu Val Tyr Lys
    1580            1585             1590

Asp Gly Ser Pro Cys Pro Ser Lys Ser Gly Leu Ser Tyr Lys Ser
    1595            1600             1605

Val Ile Ser Phe Val Cys Arg Pro Glu Ala Gly Pro Thr Asn Arg
    1610            1615             1620

Pro Met Leu Ile Ser Leu Asp Lys Gln Thr Cys Thr Leu Phe Phe
    1625            1630             1635

Ser Trp His Thr Pro Leu Ala Cys Glu Gln Ala Thr Glu Cys Ser
    1640            1645             1650

Val Arg Asn Gly Ser Ser Ile Val Asp Leu Ser Pro Leu Ile His
    1655            1660             1665

Arg Thr Gly Gly Tyr Glu Ala Tyr Asp Glu Ser Glu Asp Asp Ala
    1670            1675             1680

Ser Asp Thr Asn Pro Asp Phe Tyr Ile Asn Ile Cys Gln Pro Leu
    1685            1690             1695
```

-continued

Asn Pro Met His Ala Val Pro Cys Pro Ala Gly Ala Ala Val Cys
1700                1705                1710

Lys Val Pro Ile Asp Gly Pro Ile Asp Ile Gly Arg Val Ala
1715                1720                1725

Gly Pro Pro Ile Leu Asn Pro Ile Ala Asn Glu Ile Tyr Leu Asn
1730                1735                1740

Phe Glu Ser Ser Thr Pro Cys Leu Ala Asp Lys His Phe Asn Tyr
1745                1750                1755

Thr Ser Leu Ile Ala Phe His Cys Lys Arg Gly Val Ser Met Gly
1760                1765                1770

Thr Pro Lys Leu Leu Arg Thr Ser Glu Cys Asp Phe Val Phe Glu
1775                1780                1785

Trp Glu Thr Pro Val Val Cys Pro Asp Glu Val Arg Met Asp Gly
1790                1795                1800

Cys Thr Leu Thr Asp Glu Gln Leu Leu Tyr Ser Phe Asn Leu Ser
1805                1810                1815

Ser Leu Ser Thr Ser Thr Phe Lys Val Thr Arg Asp Ser Arg Thr
1820                1825                1830

Tyr Ser Val Gly Val Cys Thr Phe Ala Val Gly Pro Glu Gln Gly
1835                1840                1845

Gly Cys Lys Asp Gly Gly Val Cys Leu Leu Ser Gly Thr Lys Gly
1850                1855                1860

Ala Ser Phe Gly Arg Leu Gln Ser Met Lys Leu Asp Tyr Arg His
1865                1870                1875

Gln Asp Glu Ala Val Val Leu Ser Tyr Val Asn Gly Asp Arg Cys
1880                1885                1890

Pro Pro Glu Thr Asp Asp Gly Val Pro Cys Val Phe Pro Phe Ile
1895                1900                1905

Phe Asn Gly Lys Ser Tyr Glu Glu Cys Ile Ile Glu Ser Arg Ala
1910                1915                1920

Lys Leu Trp Cys Ser Thr Thr Ala Asp Tyr Asp Arg Asp His Glu
1925                1930                1935

Trp Gly Phe Cys Arg His Ser Asn Ser Tyr Arg Thr Ser Ser Ile
1940                1945                1950

Ile Phe Lys Cys Asp Glu Asp Glu Asp Ile Gly Arg Pro Gln Val
1955                1960                1965

Phe Ser Glu Val Arg Gly Cys Asp Val Thr Phe Glu Trp Lys Thr
1970                1975                1980

Lys Val Val Cys Pro Pro Lys Lys Leu Glu Cys Lys Phe Val Gln
1985                1990                1995

Lys His Lys Thr Tyr Asp Leu Arg Leu Leu Ser Ser Leu Thr Gly
2000                2005                2010

Ser Trp Ser Leu Val His Asn Gly Val Ser Tyr Tyr Ile Asn Leu
2015                2020                2025

Cys Gln Lys Ile Tyr Lys Gly Pro Leu Gly Cys Ser Glu Arg Ala
2030                2035                2040

Ser Ile Cys Arg Arg Thr Thr Thr Gly Asp Val Gln Val Leu Gly
2045                2050                2055

Leu Val His Thr Gln Lys Leu Gly Val Ile Gly Asp Lys Val Val
2060                2065                2070

Val Thr Tyr Ser Lys Gly Tyr Pro Cys Gly Gly Asn Lys Thr Ala
2075                2080                2085

Ser Ser Val Ile Glu Leu Thr Cys Thr Lys Thr Val Gly Arg Pro
2090                2095                2100

```
Ala Phe Lys Arg Phe Asp Ile Asp Ser Cys Thr Tyr Tyr Phe Ser
    2105                2110                2115

Trp Asp Ser Arg Ala Ala Cys Ala Val Lys Pro Gln Glu Val Gln
    2120                2125                2130

Met Val Asn Gly Thr Ile Thr Asn Pro Ile Asn Gly Lys Ser Phe
    2135                2140                2145

Ser Leu Gly Asp Ile Tyr Phe Lys Leu Phe Arg Ala Ser Gly Asp
    2150                2155                2160

Met Arg Thr Asn Gly Asp Asn Tyr Leu Tyr Glu Ile Gln Leu Ser
    2165                2170                2175

Ser Ile Thr Ser Ser Arg Asn Pro Ala Cys Ser Gly Ala Asn Ile
    2180                2185                2190

Cys Gln Val Lys Pro Asn Asp Gln His Phe Ser Arg Lys Val Gly
    2195                2200                2205

Thr Ser Asp Lys Thr Lys Tyr Tyr Leu Gln Asp Gly Asp Leu Asp
    2210                2215                2220

Val Val Phe Ala Ser Ser Ser Lys Cys Gly Lys Asp Lys Thr Lys
    2225                2230                2235

Ser Val Ser Ser Thr Ile Phe Phe His Cys Asp Pro Leu Val Glu
    2240                2245                2250

Asp Gly Ile Pro Glu Phe Ser His Glu Thr Ala Asp Cys Gln Tyr
    2255                2260                2265

Leu Phe Ser Trp Tyr Thr Ser Ala Val Cys Pro Leu Gly Val Gly
    2270                2275                2280

Phe Asp Ser Glu Asn Pro Gly Asp Gly Gln Met His Lys Gly
    2285                2290                2295

Leu Ser Glu Arg Ser Gln Ala Val Gly Ala Val Leu Ser Leu Leu
    2300                2305                2310

Leu Val Ala Leu Thr Cys Cys Leu Leu Ala Leu Leu Tyr Lys
    2315                2320                2325

Lys Glu Arg Arg Glu Thr Val Ile Ser Lys Leu Thr Thr Cys Cys
    2330                2335                2340

Arg Arg Ser Ser Asn Val Ser Tyr Lys Tyr Ser Lys Val Asn Lys
    2345                2350                2355

Glu Glu Glu Thr Asp Glu Asn Glu Thr Glu Trp Leu Met Glu Glu
    2360                2365                2370

Ile Gln Leu Pro Pro Arg Gln Gly Lys Glu Gly Gln Glu Asn
    2375                2380                2385

Gly His Ile Thr Thr Lys Ser Val Lys Ala Leu Ser Ser Leu His
    2390                2395                2400

Gly Asp Asp Gln Asp Ser Glu Asp Glu Val Leu Thr Ile Pro Glu
    2405                2410                2415

Val Lys Val His Ser Gly Arg Gly Ala Gly Ala Glu Ser Ser His
    2420                2425                2430

Pro Val Arg Asn Ala Gln Ser Asn Ala Leu Gln Glu Arg Glu Asp
    2435                2440                2445

Asp Arg Val Gly Leu Val Arg Gly Glu Lys Ala Arg Lys Gly Lys
    2450                2455                2460

Ser Ser Ser Ala Gln Gln Lys Thr Val Ser Thr Lys Leu Val
    2465                2470                2475

Ser Phe His Asp Asp Ser Asp Glu Asp Leu Leu His Ile
    2480                2485                2490
```

<210> SEQ ID NO 2
<211> LENGTH: 9090
<212> TYPE: DNA
<213> ORGANISM: H. sapiens

<400> SEQUENCE: 2

| | | | | | |
|---|---|---|---|---|---|
| cgagcccagt | cgagccgcgc | tcacctcggg | ctcccgctcc | gtctccacct | ccgcctttgc | 60 |
| cctggcggcg | cgaccccgtc | ccggcgcggc | ccccagcagt | cgcgcgccgt | tagcctcgcg | 120 |
| cccgccgcgc | agtccgggcc | cggcgcgatg | ggggccgccg | ccggccggag | ccccacctg | 180 |
| gggcccgcgc | ccgcccgccg | cccgcagcgc | tctctgctcc | tgctgcagct | gctgctgctc | 240 |
| gtcgctgccc | cggggtccac | gcaggcccag | gccgccccgt | tccccgagct | gtgcagttat | 300 |
| acatgggaag | ctgttgatac | caaaaataat | gtactttata | aaatcaacat | ctgtggaagt | 360 |
| gtggatattg | tccagtgcgg | gccatcaagt | gctgtttgta | tgcacgactt | gaagacacgc | 420 |
| acttatcatt | cagtgggtga | ctctgttttg | agaagtgcaa | ccagatctct | cctggaattc | 480 |
| aacacaacag | tgagctgtga | ccagcaaggc | acaaatcaca | gagtccagag | cagcattgcc | 540 |
| ttcctgtgtg | ggaaaaccct | gggaactcct | gaatttgtaa | ctgcaacaga | atgtgtgcac | 600 |
| tactttgagt | ggaggaccac | tgcagcctgc | aagaaagaca | tatttaaagc | aaataaggag | 660 |
| gtgccatgct | atgtgtttga | tgaagagttg | aggaagcatg | atctcaatcc | tctgatcaag | 720 |
| cttagtggtg | cctacttggt | ggatgactcc | gatccgacac | cttctctatt | catcaatgtt | 780 |
| tgtagagaca | tagacacact | acgagaccca | ggttcacagc | tgcgggcctg | tccccccggc | 840 |
| actgccgcct | gcctggtaag | aggacaccag | gcgtttgatg | ttggccagcc | ccgggacgga | 900 |
| ctgaagctgg | tgcgcaagga | caggcttgtc | ctgagttacg | tgagggaaga | ggcaggaaag | 960 |
| ctagactttt | tgtgatggtca | cagccctgcg | gtgactatta | catttgtttg | cccgtcggag | 1020 |
| cggagagagg | gcaccattcc | caaactcaca | gctaaatcca | actgccgcta | tgaaattgag | 1080 |
| tggattactg | agtatgcctg | ccacagagat | tacctggaaa | gtaaaacttg | ttctctgagc | 1140 |
| ggcgagcagc | aggatgtctc | catagacctc | acaccacttg | cccagagcgg | aggttcatcc | 1200 |
| tatatttcag | atggaaaaga | atatttgttt | tatttgaatg | tctgtggaga | aactgaaata | 1260 |
| cagttctgta | ataaaaaaca | agctgcagtt | tgccaagtga | aaaagagcga | tacctctcaa | 1320 |
| gtcaaagcag | caggaagata | ccacaatcag | accctccgat | attcggatgg | agacctcacc | 1380 |
| ttgatatatt | ttggaggtga | tgaatgcagc | tcagggtttc | agcggatgag | cgtcataaac | 1440 |
| tttgagtgca | ataaaaccgc | aggtaacgat | gggaaaggaa | ctcctgtatt | cacaggggag | 1500 |
| gttgactgca | cctacttctt | cacatgggac | acggaatacg | cctgtgttaa | ggagaaggaa | 1560 |
| gacctcctct | gcggtgccac | cgacgggaag | aagcgctatg | acctgtccgc | gctggtccgc | 1620 |
| catgcagaac | cagagcagaa | ttgggaagct | gtggatggca | gtcagacgga | aacagagaag | 1680 |
| aagcattttt | tcattaatat | ttgtcacaga | gtgctgcagg | aaggcaaggc | acgagggtgt | 1740 |
| cccgaggacg | cggcagtgtg | tgcagtggat | aaaaatggaa | gtaaaaatct | gggaaaattt | 1800 |
| atttcctctc | ccatgaaaga | gaaggaaac | attcaactct | cttattcaga | tggtgatgat | 1860 |
| tgtggtcatg | gcaagaaaat | taaaactaat | atcacacttg | tatgcaagcc | aggtgatctg | 1920 |
| gaaagtgcac | cagtgttgag | aacttctggg | gaaggcggtt | gctttttatga | gtttgagtgg | 1980 |
| cgcacagctg | cggcctgtgt | gctgtctaag | acagaagggg | agaactgcac | ggtctttgac | 2040 |
| tcccaggcag | ggttttctttt | tgacttatca | cctctcacaa | agaaaaatgg | tgcctataaa | 2100 |
| gttgagacaa | agaagtatga | cttttatata | aatgtgtgtg | gccggtgtc | tgtgagcccc | 2160 |
| tgtcagccag | actcaggagc | ctgccaggtg | gcaaaaagtg | atgagaagac | ttggaacttg | 2220 |

```
ggtctgagta atgcgaagct ttcatattat gatgggatga tccaactgaa ctacagaggc    2280
ggcacaccct ataacaatga agacacaca ccgagagcta cgctcatcac ctttctctgt     2340
gatcgagacg cggagtggg cttccctgaa tatcaggaag aggataactc cacctacaac     2400
ttccggtggt acaccagcta tgcctgcccg gaggagcccc tggaatgcgt agtgaccgac    2460
ccctccacgc tggagcagta cgacctctcc agtctggcaa atctgaagg tggccttgga    2520 ggaaactggt atgccatgga caactcaggg gaacatgtca cgtggaggaa atactacatt    2580
aacgtgtgtc ggcctctgaa tccagtgccg ggctgcaacc gatatgcatc ggcttgccag    2640
atgaagtatg aaaagatca gggctccttc actgaagtgg tttccatcag taacttggga    2700
atggcaaaga ccggcccggt ggttgaggac agcggcagcc tccttctgga atacgtgaat    2760
gggtcggcct gcaccaccag cgatggcaga cagaccacat ataccacgag gatccatctc    2820
gtctgctcca ggggcaggct gaacagccac cccatctttt ctctcaactg ggagtgtgtg    2880
gtcagtttcc tgtggaacac agaggctgcc tgtcccattc agcaacgac ggatacagac    2940 caggcttgct ctataaggga tcccaacagt ggatttgtgt ttaatcttaa tccgctaaac    3000
agttcgcaag gatataacgt ctctggcatt gggaagattt ttatgtttaa tgtctgcggc    3060
acaatgcctg tctgtgggac catcctggga aaacctgctt ctggctgtga ggcagaaacc    3120
caaactgaag agctcaagaa ttggaagcca gcaaggccag tcggaattga aaaagcctc    3180 cagctgtcca cagagggctt catcactctg acctacaaag ggcctctctc tgccaaaggt    3240
accgctgatg cttttatcgt ccgctttgtt tgcaatgatg atgtttactc agggcccctc    3300
aaattcctgc atcaagatat cgactctggg caagggatcc gaaacactta ctttgagttt    3360
gaaaccgcgt tggcctgtgt tccttctcca gtggactgcc aagtcaccga cctggctgga    3420
aatgagtacg acctgactgg cctaagcaca gtcaggaaac cttggacggc tgttgacacc    3480
tctgtcgatg ggagaaagag gactttctat ttgagcgttt gcaatcctct cccttacatt    3540
cctggatgcc agggcagcgc agtggggtct tgcttagtgt cagaaggcaa tagctggaat    3600
ctgggtgtgg tgcagatgag tccccaagcc gcggcgaatg gatctttgag catcatgtat    3660
gtcaacggtg acaagtgtgg gaaccagcgc ttctccacca ggatcacgtt tgagtgtgct    3720
cagatatcgg gctcaccagc atttcagctt caggatggtt tgagtacgt gtttatctgg    3780 agaactgtgg aagcctgtcc cgttgtcaga gtggaagggg caactgtga ggtgaaagac    3840 ccaaggcatg gcaacttgta tgacctgaag cccctgggcc tcaacgacac catcgtgagc    3900
gctggcgaat acacttatta cttccgggtc tgtgggaagc tttcctcaga cgtctgcccc    3960
acaagtgaca gtccaaggt ggtctcctca tgtcaggaaa agcgggaacc gcagggattt    4020
cacaaagtgg caggtctcct gactcagaag ctaacttatg aaaatggctt gttaaaaatg    4080
aacttcacgg gggggacac ttgccataag gtttatcagc gctccacagc catcttcttc    4140
tactgtgacc gcggcaccca gcggccagta tttctaaagg agacttcaga ttgttcctac    4200
ttgtttgagt ggcgaacgca gtatgcctgc ccaccttcg atctgactga atgttcattc    4260
aaagatgggg ctggcaactc cttcgacctc tcgtccctgt caaggtacag tgacaactgg    4320
gaagccatca ctgggacggg ggacccggag cactacctca tcaatgtctg caagtctctg    4380
gccccgcagg ctggcactga gccgtgccct ccagaagcag ccgcgtgtct gctgggtggc    4440
tccaagcccg tgaacctcgg cagggtaagg gacggacctc agtggagaga tggcataatt    4500
gtcctgaaat acgttgatgg cgacttatgt ccagatggga ttcggaaaaa gtcaaccacc    4560
atccgattca cctgcagcga gagccaagtg aactccaggc ccatgttcat cagcgccgtg    4620
```

```
gaggactgtg agtacacctt tgcctggccc acagccacag cctgtcccat gaagagcaac    4680
gagcatgatg actgccaggt caccaaccca agcacaggac acctgtttga tctgagctcc    4740
ttaagtggca gggcgggatt cacagctgct tacagcgaga aggggttggt ttacatgagc    4800
atctgtgggg agaatgaaaa ctgccctcct ggcgtggggg cctgctttgg acagaccagg    4860
attagcgtgg gcaaggccaa caagaggctg agatacgtgg accaggtcct gcagctggtg    4920
tacaaggatg ggtccccttg tccctccaaa tccggcctga gctataagag tgtgatcagt    4980
ttcgtgtgca ggcctgaggc cgggccaacc aataggccca tgctcatctc cctggacaag    5040
cagacatgca ctctcttctt ctcctggcac acgccgctgg cctgcgagca agcgaccgaa    5100
tgttccgtga ggaatggaag ctctattgtt gacttgtctc cccttattca tcgcactggt    5160
ggttatgagg cttatgatga gagtgaggat gatgcctccg ataccaaccc tgatttctac    5220
atcaatattt gtcagccact aaatcccatg cacgcagtgc cctgtcctgc cggagccgct    5280
gtgtgcaaag ttcctattga tggtccccc atagatatcg gccgggtagc aggaccacca    5340
atactcaatc caatagcaaa tgagatttac ttgaattttg aaagcagtac tccttgctta    5400
gcggacaagc atttcaacta cacctcgctc atcgcgtttc actgtaagag aggtgtgagc    5460
atgggaacgc ctaagctgtt aaggaccagc gagtgcgact ttgtgttcga atgggagact    5520
cctgtcgtct gtcctgatga agtgaggatg gatggctgta ccctgacaga tgagcagctc    5580
ctctacagct tcaacttgtc cagcctttcc acgagcacct taaggtgac tcgcgactcg    5640 cgcacctaca gcgttggggt gtgcaccttt gcagtcgggc cagaacaagg aggctgtaag    5700
gacggaggag tctgtctgct ctcaggcacc aagggggcat cctttggacg gctgcaatca    5760
atgaaactgg attacaggca ccaggatgaa gcggtcgttt taagttacgt gaatggtgat    5820
cgttgccctc cagaaaccga tgacggcgtc ccctgtgtct tccccttcat attcaatggg    5880
aagagctacg aggagtgcat catagagagc agggcgaagc tgtggtgtag cacaactgcg    5940
gactacgaca gagaccacga gtggggcttc tgcagacact caaacagcta ccggacatcc    6000
agcatcatat ttaagtgtga tgaagatgag acattgggga ggccacaagt cttcagtgaa    6060
gtgcgtgggt gtgatgtgac atttgagtgg aaaacaaaag ttgtctgccc tccaaagaag    6120
ttggagtgca aattcgtcca gaaacacaaa acctacgacc tgcggctgct ctcctctctc    6180
accgggtcct ggtccctggt ccacaacgga gtctcgtact atataaatct gtgccagaaa    6240
atatataaag ggccctggg ctgctctgaa agggccagca tttgcagaag gaccacaact    6300
ggtgacgtcc aggtcctggg actcgttcac acgcagaagc tgggtgtcat aggtgacaaa    6360
gttgttgtca cgtactccaa aggttatccg tgtggtggaa ataagaccgc atcctccgtg    6420
atagaattga cctgtacaaa gacggtgggc agacctgcat tcaagaggtt tgatatcgac    6480
agctgcactt actacttcag ctgggactcc cgggctgcct gcgccgtgaa gcctcaggag    6540
gtgcagatgg tgaatgggac catcaccaac cctataaatg caagagctt cagcctcgga    6600 gatatttatt ttaagctgtt cagagcctct ggggacatga ggaccaatgg ggacaactac    6660
ctgtatgaga tccaactttc ctccatcaca agctccagaa acccggcgtg ctctggagcc    6720
aacatatgcc aggtgaagcc caacgatcag cacttcagtc ggaaagttgg aacctctgac    6780
aagaccaagt actaccttca agacggcgat ctcgatgtcg tgtttgcctc ttcctctaag    6840
tgcggaaagg ataagaccaa gtctgtttct tccaccatct tcttccactg tgaccctctg    6900
gtggaggacg ggatccccga gttcagtcac gagactgccg actgccagta cctcttctct    6960
tggtacacct cagccgtgtg tcctctgggg gtgggctttg acagcgagaa tcccgggac     7020
```

| | | |
|---|---|---|
| gacgggcaga tgcacaaggg gctgtcagaa cggagccagg cagtcggcgc ggtgctcagc | | 7080 |
| ctgctgctgg tggcgctcac ctgctgcctg ctggccctgt tgctctacaa gaaggagagg | | 7140 |
| agggaaacag tgataagtaa gctgaccact tgctgtagga gaagttccaa cgtgtcctac | | 7200 |
| aaatactcaa aggtgaataa ggaagaagag acagatgaga atgaaacaga gtggctgatg | | 7260 |
| gaagagatcc agctgcctcc tccacggcag ggaaaggaag ggcaggagaa cggccatatt | | 7320 |
| accaccaagt cagtgaaagc cctcagctcc ctgcatgggg atgaccagga cagtgaggat | | 7380 |
| gaggttctga ccatcccaga ggtgaaagtt cactcgggca ggggagctgg ggcagagagc | | 7440 |
| tcccacccag tgagaaacgc acagagcaat gcccttcagg agcgtgagga cgatagggtg | | 7500 |
| gggctggtca ggggtgagaa ggcgaggaaa gggaagtcca gctctgcaca gcagaagaca | | 7560 |
| gtgagctcca ccaagctggt gtccttccat gacgacagcg acgaggacct cttacacatc | | 7620 |
| tgactccgca gtgcctgcag gggagcacgg agccgcggga cagccaagca cctccaacca | | 7680 |
| aataagactt ccactcgatg atgcttctat aattttgcct ttaacagaaa ctttcaaaag | | 7740 |
| ggaagagttt ttgtgatggg ggagaggtg aaggaggtca ggccccactc cttcctgatt | | 7800 |
| gtttacagtc attggaataa ggcatggctc agatcggcca cagggcggta ccttgtgccc | | 7860 |
| agggttttgc cccaagtcct catttaaaag cataaggccg gacgcatctc aaaacagagg | | 7920 |
| gctgcattcg aagaacccct tgctgcttta gtcccgatag ggtatttgac cccgatatat | | 7980 |
| tttagcattt taattctctc cccctattta ttgactttga caattactca ggtttgagaa | | 8040 |
| aaaggaaaaa aaaacagcca ccgtttcttc ctgccagcag gggtgtgatg taccagtttg | | 8100 |
| tccatcttga gatggtgagg ctgtcagtgt atggggcagc ttccggcggg atgttgaact | | 8160 |
| ggtcattaat gtgtcccctg agttggagct cattctgtct cttttctctt ttgctttctg | | 8220 |
| tttcttaagg gcacacacac gtgcgtgcga gcacacacac acatacgtgc acagggtccc | | 8280 |
| cgagtgccta ggttttggag agtttgcctg ttctatgcct ttagtcagga atggctgcac | | 8340 |
| cttttttgcat gatatcttca agcctgggcg tacagagcac atttgtcagt attttttgccg | | 8400 |
| gctggtgaat tcaaacaacc tgcccaaaga ttgatttgtg tgtttgtgtg tgtgtgtgtg | | 8460 |
| tgtgtgtgtg tgtgtgagtg gagttgaggt gtcagagaaa atgaattttt tccagatttg | | 8520 |
| gggtataggt ctcatctctt caggttctca tgataccacc tttactgtgc ttatttttt | | 8580 |
| aagaaaaaag tgttgatcaa ccattcgacc tataagaagc cttaatttgc acagtgtgtg | | 8640 |
| acttacagaa actgcatgaa aaatcatggg ccagagcctc ggccctagca ttgcacttgg | | 8700 |
| cctcatgctg gagggaggct gggcgggtac agcgcggagg aggagggagg ccaggcgggc | | 8760 |
| atggcgtgga ggaggaggga ggccgggcgg tcacagcatg gaggaggagg gaggcgctgc | | 8820 |
| tggtgttctt attctggcgg cagcgccttt cctgccatgt ttagtgaatg acttttctcg | | 8880 |
| cattgtagaa ttgtatatag actctggtgt tctattgctg agaagcaaac cgccctgcag | | 8940 |
| catccctcag cctgtaccgg tttggctggc ttgtttgatt tcaacatgag tgtattttt | | 9000 |
| aaaattgatt tttctcttca tttttttttc aatcaacttt actgtaatat aaagtattca | | 9060 |
| acaatttcaa taaaagataa attattaaaa | | 9090 |

```
<210> SEQ ID NO 3
<211> LENGTH: 140
<212> TYPE: PRT
<213> ORGANISM: Artificial sequence
<220> FEATURE:
<223> OTHER INFORMATION: Synthetic peptide

<400> SEQUENCE: 3
```

```
Asn Glu His Asp Asp Cys Gln Val Thr Asn Pro Ser Thr Gly His Leu
1               5                   10                  15

Phe Asp Leu Ser Ser Leu Ser Gly Arg Ala Gly Phe Thr Ala Ala Tyr
            20                  25                  30

Ser Glu Lys Gly Leu Val Tyr Met Ser Ile Cys Gly Glu Asn Glu Asn
        35                  40                  45

Cys Pro Pro Gly Val Gly Ala Cys Phe Gly Gln Thr Arg Ile Ser Val
    50                  55                  60

Gly Lys Ala Asn Lys Arg Leu Arg Tyr Val Asp Gln Val Leu Gln Leu
65                  70                  75                  80

Val Tyr Lys Asp Gly Ser Pro Cys Pro Ser Lys Ser Gly Leu Ser Tyr
                85                  90                  95

Lys Ser Val Ile Ser Phe Val Cys Arg Pro Glu Ala Gly Pro Thr Asn
            100                 105                 110

Arg Pro Met Leu Ile Ser Leu Asp Lys Gln Thr Cys Thr Leu Phe Phe
                115                 120                 125

Ser Trp His Thr Pro Leu Ala Cys Glu Gln Ala Thr
            130                 135                 140

<210> SEQ ID NO 4
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 4
aaaagaattc aacgagcatg atga                                          24

<210> SEQ ID NO 5
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 5
aaaacctagg ggtcgcttgc tcgcaggc                                      28

<210> SEQ ID NO 6
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 6
ctaggcatca tcaccatcac cattaag                                       27

<210> SEQ ID NO 7
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 7
ctagcttaat ggtgatggtg atgatgc                                       27

<210> SEQ ID NO 8
<211> LENGTH: 51
<212> TYPE: DNA
```

-continued

```
<213> ORGANISM: Artificial sequence
<220> FEATURE:
<223> OTHER INFORMATION: Synthetic oligonucleotide

<400> SEQUENCE: 8 ctagggtct gaacgacatc ttcgaggctc agaaaatcga atggcacgaa g          51

<210> SEQ ID NO 9
<211> LENGTH: 51
<212> TYPE: DNA
<213> ORGANISM: Artificial sequence
<220> FEATURE:
<223> OTHER INFORMATION: Synthetic oligonucleotide

<400> SEQUENCE: 9
ctagcttcgt gccattcgat tttctgagcc tcgaagatgt cgttcagacc c          51

<210> SEQ ID NO 10
<211> LENGTH: 38
<212> TYPE: DNA
<213> ORGANISM: Artificial sequence
<220> FEATURE:
<223> OTHER INFORMATION: Synthetic oligonucleotide

<400> SEQUENCE: 10
aaaaaaaaag atctcccatg aagagcaacg agcatgat                        38

<210> SEQ ID NO 11
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 11
aaaaaccggt gcaggccagc ggcgtgtg                                   28

<210> SEQ ID NO 12
<211> LENGTH: 35
<212> TYPE: DNA
<213> ORGANISM: Artificial sequence
<220> FEATURE:
<223> OTHER INFORMATION: Synthetic oligonucleotide

<400> SEQUENCE: 12
aaaaaccggt gagcccaaat cttctgacaa aactc                           35

<210> SEQ ID NO 13
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 13
aaaaaccggt tttacccgga gacagggaga gg                              32

<210> SEQ ID NO 14
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 14
gagcccaaat cttctgacaa aactcacac                                  29
```

```
<210> SEQ ID NO 15
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 15
ttcggtcgct tgctcgcagg                                            20

<210> SEQ ID NO 16
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 16
cgggattcac agctgctgcc agcgagaagg ggttgg                          36

<210> SEQ ID NO 17
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 17 ccaaccccatt ctcgctggca gcagctgtga atcccg                         36

<210> SEQ ID NO 18
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 18
cgggattcac agctgcttac gccgagaagg ggttgg                          36

<210> SEQ ID NO 19
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 19 ccaaccccatt ctcggcgtaa gcagctgtga atcccg                         36

<210> SEQ ID NO 20
<211> LENGTH: 34
<212> TYPE: DNA
<213> ORGANISM: Artificial sequence
<220> FEATURE:
<223> OTHER INFORMATION: Synthetic oligonucleotide

<400> SEQUENCE: 20
cacagctgct tacagcgcga aggggttggt ttac                            34

<210> SEQ ID NO 21
<211> LENGTH: 34
<212> TYPE: DNA
<213> ORGANISM: Artificial sequence
<220> FEATURE:
<223> OTHER INFORMATION: Synthetic oligonucleotide
```

<400> SEQUENCE: 21
gtaaaccaac cccttcgcgc tgtaagcagc tgtg 34

<210> SEQ ID NO 22
<211> LENGTH: 38
<212> TYPE: DNA
<213> ORGANISM: Artificial sequence
<220> FEATURE:
<223> OTHER INFORMATION: Synthetic oligonucleotide

<400> SEQUENCE: 22
cagctgctta cagcgaggcg gggttggttt acatgagc 38

<210> SEQ ID NO 23
<211> LENGTH: 38
<212> TYPE: DNA
<213> ORGANISM: Artificial sequence
<220> FEATURE:
<223> OTHER INFORMATION: Synthetic oligonucleotide

<400> SEQUENCE: 23
gctcatgtaa accaaccccg cctcgctgta agcagctg 38

<210> SEQ ID NO 24
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 24
cctggcgtgg gggcctgcgc tggacagacc aggattagc 39

<210> SEQ ID NO 25
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 25
gctaatcctg gtctgtccag cgcaggcccc cacgccagg 39

<210> SEQ ID NO 26
<211> LENGTH: 38
<212> TYPE: DNA
<213> ORGANISM: Artificial sequence
<220> FEATURE:
<223> OTHER INFORMATION: Synthetic oligonucleotide

<400> SEQUENCE: 26
cgtgggggcc tgctttggag cgaccaggat tagcgtgg 38

<210> SEQ ID NO 27
<211> LENGTH: 38
<212> TYPE: DNA
<213> ORGANISM: Artificial sequence
<220> FEATURE:
<223> OTHER INFORMATION: Synthetic oligonucleotide

<400> SEQUENCE: 27
ccacgctaat cctggtcgct ccaaagcagg cccccacg 38

<210> SEQ ID NO 28
<211> LENGTH: 33
<212> TYPE: DNA

```
<213> ORGANISM: Artificial sequence
<220> FEATURE:
<223> OTHER INFORMATION: Synthetic oligonucleotide

<400> SEQUENCE: 28
gcctgctttg dacaggccag gattagcgtg ggc                                 33

<210> SEQ ID NO 29
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 29
gcccacgcta atcctggcct gtccaaagca ggc                                 33

<210> SEQ ID NO 30
<211> LENGTH: 35
<212> TYPE: DNA
<213> ORGANISM: Artificial sequence
<220> FEATURE:
<223> OTHER INFORMATION: Synthetic oligonucleotide

<400> SEQUENCE: 30
gctttggaca gaccagggct agcgtgggca aggcc                               35

<210> SEQ ID NO 31
<211> LENGTH: 35
<212> TYPE: DNA
<213> ORGANISM: Artificial sequence
<220> FEATURE:
<223> OTHER INFORMATION: Synthetic oligonucleotide

<400> SEQUENCE: 31
ggccttgccc acgctagccc tggtctgtcc aaagc                               35

<210> SEQ ID NO 32
<211> LENGTH: 35
<212> TYPE: DNA
<213> ORGANISM: Artificial sequence
<220> FEATURE:
<223> OTHER INFORMATION: Synthetic oligonucleotide

<400> SEQUENCE: 32
gctttggaca gaccaggact agcgtgggca aggcc                               35

<210> SEQ ID NO 33
<211> LENGTH: 35
<212> TYPE: DNA
<213> ORGANISM: Artificial sequence
<220> FEATURE:
<223> OTHER INFORMATION: Synthetic oligonucleotide

<400> SEQUENCE: 33
ggccttgccc acgctagtcc tggtctgtcc aaagc                               35

<210> SEQ ID NO 34
<211> LENGTH: 37
<212> TYPE: DNA
<213> ORGANISM: Artificial sequence
<220> FEATURE:
<223> OTHER INFORMATION: Synthetic oligonucleotide

<400> SEQUENCE: 34
ggtgtacaag gatggggccc cttgtccctc caaatcc                             37
```

```
<210> SEQ ID NO 35
<211> LENGTH: 37
<212> TYPE: DNA
<213> ORGANISM: Artificial sequence
<220> FEATURE:
<223> OTHER INFORMATION: Synthetic oligonucleotide

<400> SEQUENCE: 35
ggatttggag ggacaagggg ccccatcctt gtacacc                            37

<210> SEQ ID NO 36
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 36
cgtgtgcagg cctgaggcca ggccaaccaa taggcc                             36

<210> SEQ ID NO 37
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 37
ggcctattgg ttggcctggc ctcaggcctg cacacg                             36

<210> SEQ ID NO 38
<211> LENGTH: 34
<212> TYPE: DNA
<213> ORGANISM: Artificial sequence
<220> FEATURE:
<223> OTHER INFORMATION: Synthetic oligonucleotide

<400> SEQUENCE: 38
cacagctgct tacagcgtga aggggttggt ttac                               34

<210> SEQ ID NO 39
<211> LENGTH: 34
<212> TYPE: DNA
<213> ORGANISM: Artificial sequence
<220> FEATURE:
<223> OTHER INFORMATION: Synthetic oligonucleotide

<400> SEQUENCE: 39
gtaaaccaac cccttcacgc tgtaagcagc tgtg                               34

<210> SEQ ID NO 40
<211> LENGTH: 34
<212> TYPE: DNA
<213> ORGANISM: Artificial sequence
<220> FEATURE:
<223> OTHER INFORMATION: Synthetic oligonucleotide

<400> SEQUENCE: 40
cacagctgct tacagcaaga aggggttggt ttac                               34

<210> SEQ ID NO 41
<211> LENGTH: 34
<212> TYPE: DNA
<213> ORGANISM: Artificial sequence
<220> FEATURE:
<223> OTHER INFORMATION: Synthetic oligonucleotide
```

```
<400> SEQUENCE: 41
gtaaaccaac cccttcttgc tgtaagcagc tgtg                                    34
```

INSULIN-LIKE GROWTH FACTOR II (IGF-II) BINDING FACTORS

RELATED APPLICATIONS

This application is continuation of U.S. patent application Ser. No. 11/990,479, filed on Feb. 14, 2008, now U.S. Pat. No. 8,293,875, which is a national stage filing under 35 U.S.C. §371 of international application PCT/GB2006/003011, filed Aug. 11, 2006, which was published under PCT Article 21(2) in English.

This invention relates to methods and materials for use in the sequestration of Insulin-like Growth Factor-II (IGF-II), for example, in the treatment of cancer.

The mammalian cation-independent mannose 6-phosphate/insulin-like growth factor II receptor (abbreviated to IGF2R) is a type I integral membrane protein and P-type lectin, with multiple functions attributable to its wide variety of known ligands (1-3). The ~270 kDa glycosylated protein consists of an N-terminal signal sequence (amino acids 1-44), 15 homologous extracytoplasmic repeating domains (amino acids 45-2313), a transmembrane region (amino acids 2314-2336) and a C-terminal cytoplasmic domain (amino acids 2337-2499) (4,5). Its 15 repeated domains are each ~147 amino acids in length and display significant similarity in amino acid sequence and disulphide distribution to each other (16-38% identity) and with the single extra-cytoplasmic domain of the cation-dependent mannose 6-phosphate receptor (CD-MPR) (14-28% identity) (5). Crystal structures have now been solved for domains 1, 2, 3 (6) and 11 (7) and show that each domain has a similar topology consisting of a flattened 9-strand β barrel, shared with the CD-MPR and avidin (8), suggesting that the 15 extracytoplasmic domains represent 15 homologous structural units. The main function of the IGF2R and the CD-MPR are the delivery of newly formed acid hydrolases, of which there are ~50, to the lysosome through binding to their mannose 6-phosphate (M6P) labelled residues (3). IGF2R also processes a number of other M6P and non-M6P labelled ligands. Domains 3, 9 and recently 5 (9) have been identified as the binding sites for the mannosylated proteins such as latent TGF-β (10), proliferin and granzyme B and the protease cathepsin. Site-directed mutagenesis studies have since established the critical interacting residues within domains 3 and 9 for mannose 6-phosphate (11, 12). Of the currently identified non-mannosylated ligands (IGF-II, retinoic acid, urokinase type plasminogen activator receptor and plasminogen) IGF-II has been by far the best studied with the binding site being localised to domain 11 (13-15).

IGF-II (7.5 kDa) is a small mitogenic peptide hormone that functions principally during embryonic growth, where its activity is tightly regulated, but is also frequently deregulated in tumours (16-18). Like IGF-I, IGF-II exerts its mitogenic affect predominantly by signalling through the IGF1R, leading to tyrosine kinase activation and stimulation of both the mitogen-activated protein (MAP) kinase and PKB/AKT signalling cascades. Downstream targets include the FOXO transcription factors, GSK3β, MDM2 and mTOR leading to up regulation of pro-growth and anti-apoptotic signals (19). In mammals, tight regulation of IGF-II activity is achieved by high affinity binding to six IGF binding proteins (IGFBP 1-6) and by binding to the IGF2R at the cell surface, leading to internalisation of IGFII and subsequent degradation within the lysosome (20-22). Previous NMR studies have established the structure of mature IGF-II (23,24) and site directed mutagenesis has been used to identify the residues F48, R49, S50, A54, L55 as being critical to the interaction with IGF2R (25,26). Although IGF-II is relatively structurally conserved, the IGF-II binding site of IGF2R is present only in mammalian species, where embryonic and placental growth regulation of IGF-II by the IGF2R also involves reciprocal imprinting of the genes coding these proteins (27). Disruption of Igf2 in the mouse results in reduced growth (60% of wild-type) from embryonic day 9-11 (28, 29), whereas mice with disruption of Igf2r exhibit fetal overgrowth and fatal cardiac hyperplasia (30,31). The growth and perinatal lethality phenotype is rescued when Igf2 is also disrupted, suggesting the principle critical function of IGF2R is the regulation of IGF-II (32). The specific functional interaction between IGF-II and IGF2R and its critical role in development has been highlighted more recently, as parthenogenetic embryos with maternal allele Igf2 expression can lead to normal development of live mice with two maternal genomes, and epigenetic suppression of Igf2r may account for large offspring syndrome following somatic cell cloning (33, 34).

Aberrant regulation of IGF-II activity has been repeatedly implicated as a common feature of tumours in both mouse and human (35). For example, increased expression of IGF-II by loss of imprinting (LOI) has been described in a plethora of tumour types including Wilms' tumour (36), colorectal carcinoma (37), rhabdomyosarcoma (38), Ewing's sarcoma (39), cervical carcinoma (40), lung carcinoma (41) and phaeochromocytoma (42). IGF2 LOI is particularly associated with increased relative risk of developing colorectal carcinoma (43, 44). IGF2R also acts as a tumour suppressor, as loss of heterozygosity of the receptor has been detected in a number of tumour types including liver, lung and head and neck tumours (45-48). Moreover, loss of function mutations of the receptor have been characterised (49), and over-expression of IGF2R causes decreased growth and increased apoptosis in tumour cell models (50-53). The crystal structure of IGF2R domain 11 has been solved at 1.4 Å resolution using anomalous scattering of sulphur (7), and has been confirmed by others (54). Domain 11 IGF2R structure reveals two hydrophobic sites on the surface of domain 11, the first that identifies the putative IGF-II binding site within the cleft of the β-barrel structure, spatially analogous to the hydrophilic sugar binding site of the CD-MPR, and a second that is implicated in domain-domain interactions (7, 55). The IGF-II binding site is formed by the β-strands A, B, C and D and the loops AB, CD and FG, with shorter loops conferring a shallower binding cavity than that of the CD-MPR. The residues Y1542, S1543, G1546 (AB loop), F1567, G1568, T1570, I1572 (CD loop), S1596, P1597, P1599 (FG loop) have been identified as being significantly solvent exposed and therefore potentially involved in the IGF-II interaction (7). Previously, Linnell et al quantified the interaction of IGF-II with IGF2R domain 10-13 expressed as a rat CD4 (domains 3 and 4) chimeric protein using surface plasmon resonance (SPR), and confirmed the enhancing activity of domain 13 to the domain 11-IGF-II interaction (15, 56).

The present inventors have identified novel mutants of the IGF-II binding domain of the Insulin-like Growth Factor 2 Receptor (IGF2R) which have enhanced binding affinity for IGF-II relative to the wild type IGF-II binding domain, but do not display any reduction in specificity.

One aspect of the invention provides an IGF-II binding domain consisting of the amino acid sequence of residues 1511 to 1650 of human IGF2R with 50 or fewer residues mutated or altered, wherein E1544 is substituted for a non-acidic residue.

The IGF-II binding domain binds IGF-II with increased affinity relative to the wild-type IGF-II binding domain (residues 1511 to 1650) of human IGF2R, for example 2 fold, 3 fold, 4 fold, 5 fold, 6 fold or 7 fold or more greater affinity. The binding of the mutant IGF-II binding domain to IGF-II may, for example, have an increased association rate ($k_{on}$) and/or a reduced dissociation rate ($k_{off}$) relative to the wild type IGF-II binding domain.

Preferably, the IGF-II binding domain shows a binding specificity which is identical or similar to the wild-type IGF-II binding domain (residues 1511 to 1650) of human IGF2R, i.e. it shows no binding or substantially no binding to IGF-I.

Human IGF2R has the amino acid sequence shown in SEQ ID NO: 1 and database entry NP_000867.1 GI: 4504611 and is encoded by the nucleotide sequence shown in SEQ ID NO: 2 and database entry (NM_000876.1 GI: 4504610). The amino acid sequence of residues 1511 to 1650 of human IGF2R is shown in SEQ ID NO: 3. Residue E1544 in the human IGF2R sequence corresponds to residue E34 of SEQ ID NO: 3. Except where otherwise stated, residue numbers set out herein refer to the position of the residue in the human IGF2R sequence shown in SEQ ID NO: 1.

A residue identified by its position in the human IGF2R sequence can easily be identified in a truncated or variant IGF2R sequence, such as the IGF-II binding domain sequence shown in SEQ ID NO: 3, or variants thereof, for example, using standard sequence alignment and analysis techniques.

Other than the substitution of a non-acidic residue at E1544, a IGF-II binding domain described herein may have 50 or fewer amino acid residues altered relative to the wild-type amino acid sequence of residues 1511 to 1650 of human IGF2R, preferably 45 or fewer, 40 or fewer, 30 or fewer, 10 or fewer, 5 or fewer or 3 or fewer.

An amino acid residue in the wild-type amino acid sequence may be altered or mutated by insertion, deletion or substitution of one or more amino acids. Such alterations may be caused by one or more of addition, insertion, deletion or substitution of one or more nucleotides in the encoding nucleic acid.

In some embodiments, residues F1567 and I1572 are not mutated, more preferably, residues F1567, T1570 and I1572 are not mutated, and most preferably residues F1567, T1570, I1572, P1597 and P1599 are not mutated i.e. a IGF-II binding domain described herein comprises F1567, T1570, I1572, P1597 and P1599 (which correspond to residues F57, T60, I62, P87 and P89 of SEQ ID NO: 3, respectively). Preferably, the mutant IGF-II domain retains the beta-barrel structure of the wild-type domain.

In some preferred embodiments, the IGF-II binding domain may consist of the amino acid sequence of residues 1511 to 1650 of human IGF2R with residue E1544 mutated by substitution for a non-acidic residue.

The mutant IGF-II binding domain may share at least 50% sequence identity with the wild-type amino acid sequence of residues 1511 to 1650 of human IGF2R, at least 55%, at least 60%, at least 65%, at least 70%, at least about 80%, at least 90%, at least 95% or at least 98%. The sequence may share at least 60% similarity with the wild-type sequence, at least 70% similarity, at least 80% similarity, at least 90% similarity, at least 95% similarity or at least 99% similarity.

Sequence similarity and identity are commonly defined with reference to the algorithm GAP (Wisconsin GCG package, Accelerys Inc, San Diego USA). GAP uses the Needleman and Wunsch algorithm to align two complete sequences that maximizes the number of matches and minimizes the number of gaps. Generally, default parameters are used, with a gap creation penalty=12 and gap extension penalty=4. Use of GAP may be preferred but other algorithms may be used, e.g. BLAST (which uses the method of Altschul et al. (1990) *J. Mol. Biol.* 215: 405-410), FASTA (which uses the method of Pearson and Lipman (1988) *PNAS USA* 85: 2444-2448), or the Smith-Waterman algorithm (Smith and Waterman (1981) *J. Mol. Biol.* 147: 195-197), or the TBLASTN program, of Altschul et al. (1990) supra, generally employing default parameters. In particular, the psi-Blast algorithm may be used (Nucl. Acids Res. (1997) 25 3389-3402). Sequence identity and similarity may also be determined using Genomequest™ software (Gene-IT, Worcester Mass. USA).

Sequence comparisons are preferably made over the full-length of the relevant sequence described herein.

Similarity allows for "conservative variation", i.e. substitution of one hydrophobic residue such as isoleucine, valine, leucine or methionine for another, or the substitution of one polar residue for another, such as arginine for lysine, glutamic for aspartic acid, or glutamine for asparagine.

In the mutant IGF-II binding domain, residue E1544 may be substituted for a non-acidic residue, for example, a residue other than E or D, preferably a residue other than E, D, N or Q, most preferably a residue other than E, D, N, P or G, i.e. the IGF-II binding domain may comprise an amino acid other than E, D, N, P or G at position 1544 (position 34 in SEQ ID NO: 3).

For example, residue E1544 may be substituted for an aliphatic residue such as A, V, L or I, a basic residue such as K, R or H, a sulphur containing residue such as C or M, or a hydroxyl residue, such as S or T may be used. More preferably, E1544 may be substituted for a polar residue, such as S, or a basic residue, such as K, R or H. For example, the IGF-II binding domain may comprise K, R, H or S at position 1544 (position 34 in SEQ ID NO: 3). Most preferably, E1544 is substituted for R or K.

An IGF-II binding domain as described herein may comprise one or more non-natural amino acids, modified amino acids or d-amino acids. The use of such amino acids is well-known to those of skill in the art.

A mutant IGF-II binding domain as described above may be comprised within a polypeptide.

In some embodiments, the mutant IGF-II binding domain may be linked to amino acid sequences which are not linked to the wild-type IGF-II binding domain (domain 11) of IGF2R in nature (i.e. heterologous sequences).

In some embodiments, the polypeptide may comprise multiple IGF-II binding domains, including, for example, one or more mutant IGF2 binding domains as described herein. A polypeptide may comprise two, three, four or more IGF-II binding domains. The presence of multiple domains may increase the ability of the polypeptide to bind to IGF-II. The domains may be identical (i.e. copies) or may be non-identical (i.e. they may differ at one or more amino acid residues).

The IGF-II binding domains may be directly connected without linkers or may be linked by amino acid sequences from human IGF2R, synthetic amino acid sequences, synthetic organic molecules or polypeptides that multi-merise or assemble into polymeric structures. In some embodiments, the IGF2 binding domains may be linked via biotin-streptavidin tags.

The polypeptide may further comprise one or more amino acid sequences additional to the one or more IGF-II binding domains. For example, the IGF-II binding polypeptide may comprise one or more additional domains. Additional domains may include domains of human IGF2R, such as domain 13(residues 1800 to 1991 of the IGF2R sequence), and domain 12 (residues 1651 to 1799 of the IGF2R sequence) or domains from other polypeptides (i.e. heterologous domains) which improve the stability, pharmacokinetic, targeting, affinity, purification and production properties of the polypeptide, such as an immunoglobulin Fc domain, which confers improved stability/pharmacokinetic parameters in biological fluid.

In some embodiments, the polypeptide may comprise an immunoglobulin Fc domain. Suitable immunoglobulin Fc domains are well-known in the art and include the human IgG1 Fc domain. The immunoglobulin Fc domain may be located at the N-terminal or C-terminal end of the IGF-II binding domain.

The immunoglobulin Fc domain and the IGF-II binding domain may be attached directly or via a linker molecule, for example a linker peptide.

Examples of polypeptides comprising an immunoglobulin Fc domain are shown in FIG. 8.

In preferred embodiments, the polypeptide is not comprised within a full-length IGF2R polypeptide.

In some embodiments, the polypeptide may comprise an affinity tag, which may, for example, be useful for purification. An affinity tag is a heterologous peptide sequence which forms one member of a specific binding pair. Polypeptides containing the tag may be purified by the binding of the other member of the specific binding pair to the polypeptide, for example in an affinity column. For example, the tag sequence may form an epitope which is bound by an antibody molecule.

Suitable affinity tags include for example, glutathione-S-transferase, (GST), maltose binding domain (MBD), MRGS $(H)_6$, DYKDDDDK (FLAG™), T7-, S— (KETAAAKFERQHMDS), poly-Arg ($R_{5-6}$), poly-His ($H_{2-10}$), poly-Cys ($C_4$) poly-Phe ($F_{11}$) poly-Asp($D_{5-16}$), Strept-tag II (WSHPQFEK), c-myc (EQKLISEEDL), Influenza-HA tag (Murray, P. J. et al (1995) *Anal Biochem* 229, 170-9), Glu-Glu-Phe tag (Stammers, D. K. et al (1991) *FEBS Lett* 283, 298-302), Tag.100 (Qiagen; 12 aa tag derived from mammalian MAP kinase 2), Cruz tag 09™ (MKAEFRRQESDR, Santa Cruz Biotechnology Inc.) and Cruz tag 22™ (MRDALDRLDRLA, Santa Cruz Biotechnology Inc.). Known tag sequences are reviewed in Terpe (2003) Appl. Microbiol. Biotechnol. 60 523-533.

In preferred embodiments, a poly-His tag such as $(H)_6$ or MRGS$(H)_6$ may be used.

The affinity tag sequence may be removed after purification, for example, using site-specific proteases.

In some embodiments, the protein may be coupled to an appropriate signal leader peptide to direct secretion of the fusion polypeptide from cell into the culture medium. A range of suitable signal leader peptides are known in the art. The signal leader peptide may be heterologous to the IGF binding domain i.e. it may be a non-IGF2R signal sequence. For example, an α-factor secretion signal or BiP signal sequence may be employed. Preferably, the signal peptide is removed by post-translational processing after expression of the polypeptide.

Preferably, the polypeptide comprising or consisting of one or more IGF-II binding domains is soluble. A soluble polypeptide does not naturally associate with membranes after expression and does not form aggregates in aqueous solution under physiological conditions. A soluble polypeptide may, for example, lack a transmembrane domain.

Another aspect of the invention provides a nucleic acid encoding a polypeptide comprising or consisting of one or more mutant IGF-II binding domains as described herein.

Nucleic acid encoding a polypeptide may be comprised in a vector. Suitable vectors can be chosen or constructed, containing appropriate regulatory sequences, including promoter sequences, terminator fragments, polyadenylation sequences, enhancer sequences, marker genes and other sequences as appropriate. Preferably, the vector contains appropriate regulatory sequences to drive the expression of the nucleic acid in mammalian cells. A vector may also comprise sequences, such as origins of replication and selectable markers, which allow for its selection and replication in bacterial hosts such as *E. coli*.

Vectors may be plasmids, viral e.g. 'phage, or phagemid, as appropriate. For further details see, for example, Molecular Cloning: a Laboratory Manual: 3rd edition, Russell et al., 2001, Cold Spring Harbor Laboratory Press. Many known techniques and protocols for manipulation of nucleic acid, for example in preparation of nucleic acid constructs, mutagenesis, sequencing, introduction of DNA into cells and gene expression, are described in detail in Current Protocols in Molecular Biology, Ausubel et al. eds. John Wiley & Sons, 1992.

A nucleic acid or vector as described herein may be introduced into a host cell.

A range of host cells suitable for the production of recombinant polypeptides are known in the art. Suitable host cells may include prokaryotic cells, in particular bacteria such as *E. coli*, and eukaryotic cells, including mammalian cells such as CHO and CHO-derived cell lines (Lec cells), HeLa, COS, and HEK293 cells, amphibian cells such as *Xenopus oocytes*, insect cells such as *Trichoplusia ni*, Sf9 and Sf21 and yeast cells, such as *Pichia pastoris*.

Techniques for the introduction of nucleic acid into cells are well established in the art and any suitable technique may be employed, in accordance with the particular circumstances. For eukaryotic cells, suitable techniques may include calcium phosphate transfection, DEAE-Dextran, electroporation, liposome-mediated transfection and transduction using retrovirus or other virus, e.g. adenovirus, AAV, lentivirus or vaccinia. For bacterial cells, suitable techniques may include calcium chloride transformation, electroporation and transfection using bacteriophage.

Marker genes such as antibiotic resistance or sensitivity genes may be used in identifying clones containing nucleic acid of interest, as is well-known in the art.

The introduced nucleic acid may be on an extra-chromosomal vector within the cell or the nucleic acid may be integrated into the genome of the host cell. Integration may be promoted by inclusion of sequences within the nucleic acid or vector which promote recombination with the genome, in accordance with standard techniques.

The introduction may be followed by expression of the nucleic acid to produce the encoded polypeptide comprising or consisting of one or more mutant IGF2 binding domains. In some embodiments, host cells (which may include cells actually transformed although more likely the cells will be descendants of the transformed cells) may be cultured in vitro under conditions for expression of the nucleic acid, so that the encoded IGF2 binding polypeptide is produced. When an inducible promoter is used, expression may require the activation of the inducible promoter.

The expressed polypeptide comprising or consisting of one or more mutant IGF-II binding domains may be isolated and/or purified, after production. This may be achieved using any convenient method known in the art. Techniques for the purification of recombinant polypeptides are well known in the art and include, for example HPLC, FPLC or affinity chromatography. In some embodiments, purification may be performed using an affinity tag on the polypeptide as described above.

Polypeptides comprising or consisting of one or more mutant IGF2 binding domains which are produced as described may be investigated further, for example the pharmacological properties and/or activity may be determined. Methods and means of protein analysis are well-known in the art.

Another aspect of the invention provides a polypeptide comprising or consisting of one or more IGF-II binding domains, a nucleic acid, or a host cell as described herein for use in a method of treatment of the human or animal body by therapy. For example, the polypeptide comprising an IGF2 binding domain, nucleic acid or host cell as described herein may be used in a method of treatment of cancer.

Another aspect of the invention provides the use of a polypeptide comprising or consisting of one or more IGF-II binding domains, a nucleic acid, or a host cell as described herein in the manufacture of a medicament for use in the treatment of cancer.

Cancers which may be treated as described herein include cancers characterised by up-regulation of IGF-II, for example colorectal cancers such as intestinal adenoma and colorectal carcinoma, cervical cancers such as cervical carcinoma, lung cancers such as lung carcinoma, kidney cancers such as Wilms' tumour, muscle cancers such as rhabdomyosarcoma, bone cancers such as Ewing's sarcoma, endocrine cancers such as phaeochromocytoma, liver cancers such as hepatocellular carcinoma, brain tumours such as glioblastoma, breast cancers such as inflammatory breast cancers, upper gastrointestinal cancers such as pancreatic cancer, haematological cancers such as myeloma, soft tissue sarcomas such as haemangiopericytoma and cancers that result in tumour related hypoglycaemia related to increased circulating levels of IGF2 and/or express the IGF-II gene at high levels.

Polypeptides as described herein may also be useful as cancer-targeting agents to deliver other anti-cancer molecules to tumours, radiolabels to detect and treat tumours, and sensitising agents that sensitise tumours to other cancer therapies, including chemotherapy and radiotherapy.

Whilst a polypeptide comprising or consisting of one or more IGF2 binding domains, a nucleic acid, or a host cell as described herein may be administered alone, it is preferable to present it as a pharmaceutical composition (e.g. formulation) which comprises the polypeptide, nucleic acid or cell, together with one or more pharmaceutically acceptable carriers, adjuvants, excipients, diluents, fillers, buffers, stabilisers, preservatives, lubricants, or other materials well known to those skilled in the art and, optionally, other therapeutic or prophylactic agents.

Methods of the invention may therefore comprise the step of formulating a polypeptide comprising or consisting of one or more IGF2 binding domains, a nucleic acid, or a host cell as described herein with a pharmaceutically acceptable carrier, adjuvant or excipient.

The term "pharmaceutically acceptable" as used herein pertains to compounds, materials, compositions, and/or dosage forms which are, within the scope of sound medical judgement, suitable for use in contact with the tissues of a subject (e.g., human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation. The precise nature of the carrier or other material will depend on the route of administration, which may be oral, or by injection, e.g. cutaneous, subcutaneous or intravenous.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, or Lactated Ringer's Injection. Preservatives, stabilisers, buffers, antioxidants and/or other additives may be included, as required.

Suitable carriers, excipients, etc. can be found in standard pharmaceutical texts, for example, Remington's Pharmaceutical Sciences, 18th edition, Mack Publishing Company, Easton, Pa., 1990.

The pharmaceutical compositions and formulations may conveniently be presented in unit dosage form and may be prepared by any methods well known in the art of pharmacy. Such methods include the step of bringing into association the IGF-II binding polypeptide, nucleic acid or host cell with the carrier which constitutes one or more accessory ingredients. In general, the compositions are prepared by uniformly and intimately bringing into association the active compound with liquid carriers or finely divided solid carriers or both, and then if necessary shaping the product.

Whether it is an IGF-II binding domain or polypeptide, nucleic acid or host cell according to the present invention that is to be given to an individual, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors.

A composition may be administered alone or in combination with other treatments, either simultaneously or sequentially dependent upon the circumstances of the individual to be treated.

Various further aspects and embodiments of the present invention will be apparent to those skilled in the art in view of the present disclosure. All documents mentioned in this specification are incorporated herein by reference in their entirety.

The definitions and descriptions of the features set out above apply to all aspects and embodiments which comprise those features, unless context dictates otherwise.

Certain aspects and embodiments of the invention will now be illustrated by way of example and with reference to the figures and tables described below.

FIG. 1 shows sensorgrams obtained from varying approaches for the analysis of IGF-II binding to domain 11 by SPR. SPR experiments conducted using either domain 11 (a, b, c) or IGF-II (d, e, f) as the immobilized ligand. Duplicate samples of IGF-II at 268, 134, 67, 33.5, 17.8, 8.4, 4.2 and 2.1 nM injected over biotinylated CD4-11 from 293T cells (a), amine coupled domain 11 from E. coli (b) and biotinylated domain 11 from yeast (c). Biotinylated IGF-II immobilised to the chip, analyte injections of crude CD4-11 at 240, 120, 60, 30, 15, 7.5 and 3.8 nM (d), purified 11 from E. coli at 4096, 2048, 1024, 512, 256, 128, 64, 32, 16 and 8 nM (note 4096 and 2048 nM traces overlap in this example) (e) and purified 11 from yeast at 4096, 2048, 1024, 512, 256, 128, 64, 32, 16 and 8 nM (f).

FIG. 2 shows the IGF-II binding site of domain 11 and the location of mutated residues. FIG. 2(a) shows the primary amino acid sequence of IGF2R domain 11 (amino acids 1511-1650). The loop regions that form the hydrophobic patch of the putative IGF-II binding site are boxed and the candidate interacting residues that were mutated in this study are shown in bold. The nature of each mutated residue is indicated above (a=acidic, b=basic, h=hydrophobic and p=polar). FIG. 2(b) shows the region of domain 11 encompassing the mutated residues (underlined in a) and the specific mutations generated.

FIG. 3 shows a diagram of a domain 11 fusion proteins (wild type or carrying site-directed mutants) with C-terminal His$_6$ tag and N-terminal a-factor secretion signal. The expressed domain 11 consists of amino acids 1511-1650 of IGF2R. Cleavage of the α-factor signal (at the site indicated by the arrow) during secretion generates the final soluble 17 kDa protein.

FIG. 4 shows sensorgrams obtained from SPR analysis of wild type and mutated IGF2R domain 11 constructs binding to IGF-II. Sensorgrams were obtained after injections of wild type domain 11 (a) or domain 11 carrying the following single-residue alterations: in loop AB, Y1542A (b), S1543A (c), E1544A (d) and K1545A (e), in loop CD, F1567A (f), Q1569A (g), T1570A (h), I1572A (i) and I1572T (j) in loop FG, S1596A (k) or in loop GH, G1619R (l). For all except (f), (i) and (j), duplicate analyte injections were performed at concentrations of 4096, 2048, 1024, 512, 256, 128, 64, 32, 16 and 8 nM. For (f), (i) and (j) analyte was injected at 16384, 8192, 4096, 2048, 1024, 512, 256, 128, 64 and 32 nM. Inspection of the sensorgrams show that the mutations F1567A (f), I1572A (i) and I1572T (j) all but abolish IGF-II binding, S1543A (c), Q1569A (g) and S1596A (k) have little affect and Y1542A (b) and T1570A (h) have an intermediate impact. The polymorphism G1619R (l) has an apparent wild type interaction and the E1544A (d) mutation has a modest positive affect on IGF-II binding.

FIG. 5 shows sensorgrams obtained from SPR analysis of wild type domain 11 and mutants at position 1544 interacting with Sensorgrams were obtained after injections of wild type domain 11 (a) or domain 11 mutants with the following substitutions at position 1544: E1544A (b), E1544V (c), E1544K (d). Duplicate analyte injections were performed at concentrations of 4096, 2048, 1024, 512, 256, 128, 64, 32, 16 and 8 nM. The sensorgrams for E1544A (b) and E1544V (c) show a modest but visible increase in affinity over the wild type (a), whereas E1544K (d) clearly shows a marked increase in affinity, with an obvious decrease in dissociation rate (see Table 4).

FIG. 6 shows analysis of the binding of wild type and E1544A domain 11 to IGF-II by Isothermal Titration calorimetry FIG. 6(a) shows enthalpic heat released per second for the Blank (offset by +0.05/cal/sec), 11 (offset by −0.2 μcal/sec) and E1544A. FIG. 6(b) shows integrated binding isotherms for the titrations of IGF-II into domain 11 (offset by −4 kcal/mol) and the E1544A mutant, after blank subtraction. Fitting of the experimental data to a single site model (red line) generated KDvalues of 150±4.4 nM for domain 11 and 81±8.8 nM for E1544A. Values are the mean±S.E. of duplicate experiments.

FIG. 7 shows a histogram showing steady-state affinities CM obtained from domain 11 constructs specifically mutated to replace the glutamate residue at position 1544 with the indicated amino acid. The affinity of the wildtype (WT) domain 11 has been included for comparison. Individual columns are shaded to reflect the property of the introduced residue (dots=hydrophobic, unshaded=polar, shaded=basic, diagonal lines=acidic). Bars=standard error of mean.

FIG. 8 shows Domain 11 of human IGF2R cloned into the expression vectors pPIC9K and pMT/BiP/V5-His B; the latter vector including a C-terminal human IgG1 Fc tag for dimerisation.

FIG. 9 shows that increased doses of IGF-II lead to an increase in phosphorylation of PKB in HaCaT cell lines. Samples were probed with an anti-phospho-(Ser473) PKB antibody. Equal loading was confirmed by re-probing the blot with an antibody to α-tubulin FIG. 10 shows that increased doses of IGF-II lead to an increase in phosphorylation of PKB in immortalised mouse embryonic fibroblasts (MEF) homozygous null for Igf2 (Igf2$^{-/-}$) and HaCaT cell lines.

Figure 1:
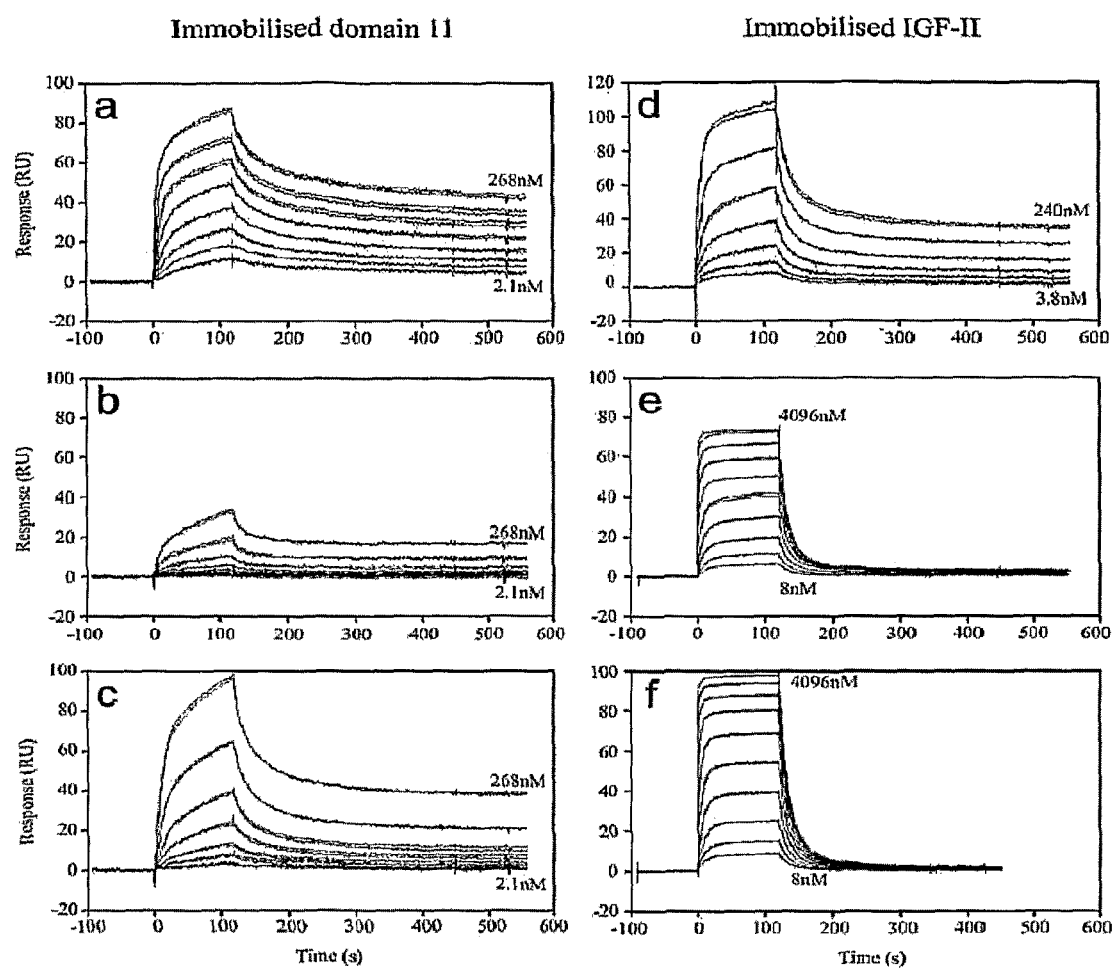

Table 1 shows the oligonucleotide primers which were used to generate site-directed mutants. The sequence of the forward and reverse oligonucleotide primer pairs used for site-directed mutagenesis to generate domain 11 constructs encoding single residue changes. Bold type indicates the altered codon and the mutated bases are shown in lower case. (NM_000876.1 GI: 4504610 Human IGF2R).

Table 2 shows the SPR kinetic data for the interaction of IGF2 with domain 11 purified from either *E. coli* or *Pichia pastoris*. Values are the mean±S.E.M. of three separate experiments.

Table 3 shows kinetic data obtained from SPR analysis of domain 11 mutants interacting with IGF2. Relative affinity was calculated by dividing steady-state values for KD by that obtained from the wild type domain 11 receptor. Values are the mean±S.E.M. of three separate experiments.

Table 4 shows kinetic data obtained from SPR analysis of domain 11 mutated at position 1544 interacting with IGF2. Values are the mean±S.E.M. of three separate experiments.

Table 5 shows kinetic data obtained from SPR analysis of domain 11 in which E1544 was replaced with all possible amino acid residues.

Table 6 shows a comparison of IGF2 dissociation affinity constants ($K_D$) of selected domain 11 constructs determined using either Biacore or ITC Table 7 shows the calculated masses, isoelectric points, and molar extinction coefficients of the IGF2R domain 11 proteins described herein.

Table 8 shows kinetic and affinity constants for IGF2 binding to IGF2R domain 11 proteins described herein.

EXPERIMENTS

Methods

Construction of Plasmids for Expression of IGF2R Domain 11 and Site-Directed Mutants Domain 11 of IGF2R was amplified by PCR from the pEFBOS plasmid containing domains 10-13 previously described by Linnell et al (15) and derived from ATCC (J03528), using primers 11EF (5'-AAAAGAATTCAAC-GAGCATGATGA-3') (SEQ ID NO: 4) and 11AR (5'-AAAACCTA GGGGTCGCTTGCTCGCAGGC-3') (SEQ ID NO: 5) incorporating EcoRI and AvrII restriction sites respectively. The product was blunt-end ligated into the pCR-Blunt vector (Invitrogen) to generate pCR-11. Mutant constructs encoding single-residue changes were generated using the QuikChange II Site-directed Mutagenesis kit (Stratagene) according to the manufacturer's protocols, using pCR-11 as template and primer pairs as shown in Table 1. The desired mutations were confirmed by DNA bidirectional sequencing performed by The Sequencing Service (School of Life Sciences, University of Dundee, Scotland, www.dnaseq.co.uk) using Applied Biosystems Big-Dye Ver 3.1 chemistry on an Applied Biosystems model 3730 automated capillary DNA sequencer.

Wild type and mutant constructs were excised with EcoRI and AvrII for cloning into the *Pichia pastoris* expression vector pPIC-HIS, generating pPIC-11 (either wild type or with the indicated mutation). The pPIC-HIS vector used in this study was derived from Invitrogen's pPIC-9K expression plasmid in which high-level expression is driven from the methanol inducible AOX1 promoter and the expressed protein is targeted for secretion into the growth media by fusion to the *Saccharomyces cerevisiae* mating pheromone α-factor. This signal sequence is efficiently cleaved during secretion resulting in native protein. The pPIC-HIS vector for expression of wild type and mutant domain 11 constructs was generated by altering pPIC-9K by the insertion of a double-stranded linker, formed by annealing the following oligonucleotides HISF (5'-CTAGGCATCAT CACCATCAC-CATTAAG-3') (SEQ ID NO: 6) and HISR (5'-CTAGCT-TAATGGTGATGGTGA TGATGC-3') (SEQ ID NO: 7), into the AvrII restriction site. The linker was designed such that cloning of the domain 11 constructs into the EcoRI and resultant AvrII site would result in an in-frame fusion with a C-terminal His6 tag for detection and purification. The pPIC-Bio vector for the expression in *Pichia* of domain 11 with a biotinylation motif was similarly generated by insertion of a double stranded linker, formed by annealing the following oligonucleotides;
BIOF(5'-CTAGGGGTCTGAACGACATCTTCGAG-GCTCAGAAAATCGAATGGCACGAAG) (SEQ ID NO: 8) and,
BIOR(5'-CTAGCTTCGTGCCATTCGATTTTCT-GAGCCTCGAAGATGTCGTTCAGACCC) (SEQ ID NO: 9); into the AvrII restriction site of pPIK-9K. The linker encodes the Avitag sequence for efficient labelling with biotin, using the BirA enzyme (Avidity, Denver, USA). Subsequent cloning of domain 11 into the EcoRI and AvrII restriction sites resulted in an in-frame C-terminal fusion. For IGF2R domain 11 protein expressed in bacteria, domain 11 was subcloned into pET-15 vector, expressed, protein purified and refolded as described (7).

Transformation and Expression of Domain 11 and Mutant Constructs in 293T Cells

Transfections and expression of CD4-IGF2R domain 11 constructs (wild-type and I1572T mutants) were as described (15).

Transformation and Expression of Domain 11 and Mutant Constructs in *Pichia pastoris*

Targeted integration of the expression constructs into the h is 4 locus of the *P. pastoris* genome was achieved by linearising approximately 5 μg of the relevant vector within the HIS4 gene using SalI, before transforming into the histidine auxothrophic *P. pastoris* strain GS115 (Invitrogen) by electroporation, following Invitrogen's instructions. Briefly, an overnight 5 ml yeast culture was grown in YPD (1% yeast extract, 2% peptone 2% glucose) to A600~2.0, this was diluted to A600~0.1 in 50 ml of YPD and grown until A600 reached ~1.5 (4-5 hours). After washing, cells were resuspended by adding 200 μl of 1M ice-cold sorbitol. 80 μl of the cell mixture was then added to the transforming DNA in a 0.2 cm Gene Pulser cuvette (BioRad) and electroporated at 1500 kV, 25 μF, 400Ω. 1 ml of 1M ice-cold sorbitol was immediately added to the mixture before spreading on MD (1.34% YNB, 4×10-5% biotin, 2% dextrose, 2% agar) plates to select for histidine prototrophs.

For expression, each strain was grown at 30° C., 250 r.p.m.in 250 ml conical flasks containing 50 ml of BMGY (1% yeast extract, 2% peptone, 100 mM potassium phosphate pH6.0, 1.34% YNB, 4×10-5% biotin, 1% glycerol), inoculated from a 5 ml overnight starter culture, for 24 hours (A600~6.0) IGF2R domain 11 mutagenesis and IGF-II binding kinetics before the cells were harvested by centrifugation and induced to express by being transferred to 50 ml of BMMY (1% yeast extract, 2% peptone, 100 mM potassium phosphate pH6.0, 1.34% YNB, 4×10-5% biotin, 0.5% methanol). Cultures were supplemented with methanol to a final volume of 1% after a further 24 and 48 hours, after which the cells were removed by centrifugation and the supernatant was retained. Supernatants were subjected to SDS-PAGE and analysed both by staining with coomassie and by western blot. For proteins carrying the His6 tag, blots were probed using an Anti-His6 mouse monoclonal antibody conjugated to peroxidase (Roche Diagnostics) and visualised using ECL (Amersham Biosciences).

Purification of Yeast Expressed Proteins 50 ml of yeast supernatant was passed through a 0.22 μm filter, concentrated in an Amicon Ultra centrifugal concentrator (10 kDa) and purified using a His-Bind Quick 300 Cartridge (Novagen) following the manufacturer's protocols, followed buffer exchange with (10 mM HEPES, pH 7.4, 150 mM NaCl, 3 mM EDTA, 0.005% surfactant P20).

Concentrations were determined by measuring absorbance at 280 nm and applying extinction coefficients as calculated by ProtParam (http://us.expasy.org/tools/protparam.html).

Circular Dichroism Spectroscopy

CD spectra were obtained from 0.1 mg/ml solution of protein in 10 mM sodium phosphate buffer pH 7.4 using a Jobin-Yvon CD6 spectropolarimeter, over a wavelength range from 190-250 nm across a 1 mm path length. UV spectra of 10 measurements were averaged and corrected for the solvent CD signal.

Analytical Gel Filtration

Analytical gel filtration was carried out on a Superdex 75 HR 26/60 column (Amersham Biosciences) equilibrated with HBS-E buffer, linked to an AKTA Purifier system (Amersham Biosciences). The column was calibrated with BSA (66 kDa), carbonic anhydrase (29 kDa), and cytochrome c (12.5 kDa). Purified protein was loaded at ~5 mg/ml. The molecular weight of domain 11 was determined from a plot of the Ve/Vo vs. log (MW) of the standards, where Ve is the elution volume of the protein and Vo is the void volume. The void volume for the column was determined by the elution of blue dextran (2000 kDa).

Analytical Ultracentrifugation

Sedimentation equilibrium experiments were performed in a Beckman XL-A analytical ultracentrifuge (Beckman, Palo Alto, Calif., USA) as described previously (79). Data were fitted by non-linear least-squares analysis using ORIGIN software (80), to a single value for $M_{w,app}$ using the partial specific volume calculated by SEDNTERP(80). Fits were evaluated on the basis of random variation in the residuals, where the residuals represent the difference between each data point and the corresponding theoretical point on the fitted curve.

Surface Plasmon Resonance Analysis

Kinetic analysis by Surface Plasmon Resonance (SPR) was conducted on a BIAcore 3000 biosensor (BIAcore, Uppsala, Sweden) at 25° C. in HBS-EP (10 mM HEPES, pH 7.4, 150 mM NaCl, 3 mM EDTA, 0.005% surfactant P20) at a flow rate of 40 µl/min. After preconditioning the sensor chip with 3×1 min injections of 1 M NaCl, 50 mM NaOH, approximately 50 Response Units (RU) of recombinant human Biotinyl-IGF-I or Biotinyl-IGF-II (GroPep Ltd, Adelaide, Australia) was immobilised on a Sensor Chip SA by affinity capture to streptavidin. Kinetic experiments consisted of a two minute injection of analyte followed by a 100s dissociation phase in running buffer, after which the binding surface was regenerated with a 2 minute injection of 2 M $MgCl_2$. A blank flow cell was used for in-line reference subtraction of changes due to differences in refractive index of running buffer versus sample and a buffer-only injection was used to subtract instrument noise and drift. Injections were performed in duplicate for each concentration and in a randomised order. Kinetic parameters were determined by global fitting of sensorgrams to a two-state (conformational change) binding model using BIAevaluation software version 4.0.1. In all cases the minor component made an insignificant contribution to the overall affinity and as such only the kinetic parameters of the major binding component were used. For each interaction the dissociation affinity constant ($K_D$) was also calculated by fitting of the response of each concentration at equilibrium to a steady-state affinity model using BIAevaluation. In order to investigate the influence of ionic strength, kinetic experiments were conducted in HBS-EP running buffers containing the desired NaCl concentration. In each case, analyte samples were made up in the appropriate running buffer prior to injection.

Data for thermodynamic analysis was obtained on a BIAcore T100 by conducting kinetic experiments at temperatures of 20° C., 25° C., 30° C., 37° C. and 42° C. in HBS-EP (10 mM HEPES, pH 7.4, 150 mM NaCl, 3 mM EDTA, 0.05% surfactant P20). Kinetic analysis at each temperature was conducted as above, using ~0.50 RU of immobilised biotinylated IGF2 on a SA sensor chip surface. Duplicate injections of analyte were performed at 512, 256, 128, 64, 32, 16, and 8 nM after each of which the surface was regenerated using a 2 min injection of 2 M MgCl. A blank flow cell and buffer blank injections were used for reference subtraction. The data were analysed using the BIAcore T100 evaluation wizard. Sensorgrams generated at each temperature were fit to a two-state reaction model. The derived kinetic and affinity parameters of the major component were fit to the linear forms of the van't Hoff and Eyring equations to obtain values for $\Delta H°$, $\Delta s°$, $\Delta H°^{\ddagger}$ and $\Delta S°^{\ddagger}$.

Kinetic binding experiments for Fc-tagged IGF2R domain 11 proteins were carried out at 25° C. at a 75 µl/min flow rate in HES-EP binding buffer. For kinetic assays, six concentrations of Fc-tagged IGF2R domain 11 protein were prepared by performing two-fold serial dilutions (in HBS-EP) ranging from 2.464 nM to 0.077 nM. A buffer control and a reference flow cell were included. Analytes were injected over the ligand surface for 3 min, following which the analyte solutions were replaced by HBS-EP buffer for 1 hour. Regeneration of the sensor chip for subsequent injections was accomplished by a 60 µl injection of 2M $MgCl_2$. All experiments were repeated in triplicate. Data transformation and overlay plots were prepared with BIAevaluation software version 4.0.1. The reference flow cell data were subtracted and the regeneration and air spikes deleted. Curves were x and y-transformed and the buffer control subtracted. Data was fitted simultaneously and as much association and dissociation data included as possible. Injection start and stop points were set precisely and the data fit using the bivalent analyte model for curve fitting without bulk refractive index change. Mass transfer control experiments were performed by injecting 0.616 nM $11^{E1544K}$-Fc protein at five flow rates: 5, 20, 40, 60 and 75 µl/min. Binding curves were compared for consistency.

Isothermal Titration Calorimetry

Calorimetric measurements were performed using a VP-ITC microcalorimeter (MicroCal). All solutions were thoroughly degassed before use by stirring under vacuum. Titrations were performed at 25° C. and consisted of 17×15 µl injections (after an initial 7.5 µl injection) of 40 µM IGF-II in HBS-E buffer (10 mM HEPES, pH 7.4, 150 mM NaCl, 3 mM EDTA) at a rate of 1 injection every 3 mins. The sample cell contained either wild type domain 11 (7 uM) or the E1544A mutant (8 µM), also in HBS-E buffer. To correct for the heat effects of dilution and mixing, reaction heats obtained from a control experiment, in which IGF2 was injected into HBS-E, were subtracted. calorimetric data were analysed using MicroCal ORIGIN software (version 5.0) supplied with the instrument. Thermodynamic parameters were derived by fitting the binding isotherms to a single-site binding model. Values for dissociation affinity constants (KD) were determined from duplicate experiments.

Construction of Fc Tagged IGF-II Ligand Trap Expression Vectors

Domain 11 of M6P/IGF2R cDNA was PCR amplified from plasmid pEFBOS_1-15 (17) using Pwo polymerase (Roche) and the BglII site containing forward primer Bg1-11-forward (5'-AAAAAAAAAGATCTCCCATGAAGAG-CAACGAGCATGAT-3') (SEQ ID NO: 10) and the AgeI site containing reverse primer Age-11-reverse (5'-AAAAACCG-GTGCAGGCCAGCGGCGT GTG-3') (SEQ ID NO: 11). The PCR product was desalted using Microcon YM-100 filters (Millipore) and digested with the restriction enzymes BglII and AgeI. The digested PCR product was gel purified using Geneclean (Q-BIOgene, Cambridge, UK) and cloned into BglII and AgeI double-digested, gel purified *Drosophila* expression vector pMT/BiP/V5-His B, to create pDes11. This construct was then C-terminally tagged with the human IgG1 Fc domain as a dimerisation motif. To achieve this, Fc domain cDNA was PCR amplified from IMAGE clone 4851063 (ATCC-6878978) using Pwo polymerase and the AgeI site containing primers Age-Fc-forward (5'-AAAAACCGGT-GAGCCCAAATCTTCTGACAAAACTC-3') (SEQ ID NO: 12) and Age-Fc-reverse (5'-AAAAACCGG /TTTACCCG-GAGACAGGGAGAGG-3') (SEQ ID NO: 13) according to rationale described previously (82). The PCR product was cleaned with a Microcon YM-100, digested with AgeI, purified by Geneclean and cloned into AgeI digested and CIAP dephosphorylated pDes11 to create pDes11-Fc. Orientation of the cloned Fc gene was determined by PCR using the Bg1-11-forward and Age-Fc-reverse primers. To facilitate the future cloning of 11-Fc into other expression vectors, the AgeI site linking domain 11 to the Fc tag was removed using the Stratagene ExSite mutagenesis kit and the 5' phosphorylated oligos Fc ExSite forward (5'-GAGCCCAAATCTTCT-GACAAAACTCACAC-3') (SEQ ID NO: 14) and 11 ExSite reverse (5'-TTCGGTCGCTTGCTCGCAGG-3') (SEQ ID NO: 15). Site directed null and enhanced mutant versions of domain 11 were made using the oligos and protocols described (75), namely $11^{E1544K}$ and $11^{I1572A}$. Fc-tagged domain $11^{I1572A}$ (null mutant) and Fc-tagged domain $11^{E1544}$ (enhanced mutant) expression vectors were thus generated, and were named pDes $11^{I1572A}$-Fc and pDes $11^{E1544K}$-Fc respectively. All constructs were verified by DNA sequencing, performed by the University of Dundee Sequencing Service. The proteins produced from these vectors were named 11-Fc, $11^{I1572A}$-Fc and $11^{E1544K}$-Fc.

Production of Fc-Tagged IGF-II Ligand Trap Proteins in *Drosophila melanogaster* Cells D.Mel-2 serum-free adapted *Drosophila melanogaster* Schneider 2 cells were maintained in 5 ml of Drosophila-SFM (serum-free media) supplemented with 16.5 mM L-glutamine, at 28'C in T-10 tissue culture flasks. The cells were seeded at $1 \times 10^5$ cells/ml and split when they reached $1 \times 10^7$ cells/ml. Cells were transfected at 70% confluency in a T-175 flask by complexing 48 μg of pDesII-Fc plasmid DNA with 96 μl TransFectin reagent (BioRad) according to the manufacturer's instructions. Transfected cells were cultured in 30 ml of medium total. Twenty four hours post transfection, 30 μl of 500 mM filter sterilised copper sulphate was added to induce transgene expression. The cells were maintained in culture for a further 72 hours to secrete folded protein expressed from the transgene. Sodium phosphate was then added to the cell supernatant to a final concentration of 20 mM and the pH adjusted to 7. The supernatant was filter-sterilised and Fc-tagged protein affinity purified with 3 ml ProteinA Fast Flow Sepharose (Amersham Biosciences) in a column, according to the manufacturer's instructions. Bound protein was washed with 5 column volumes of 20 mM sodium phosphate, pH 7, and eluted in 5 column volumes of 0.1 M sodium citrate, pH 3.5. The eluted protein was rapidly neutralised with 0.1 volumes of 1 M Tris, pH 9, and the pH adjusted to 7.4. Buffer exchange into PBS and protein concentration was performed using 30 kDa MWCO Amicon Ultra-15 filters. The column was regenerated with 0.1 M sodium citrate, pH 3, and stored in 20% ethanol.

Measurement of Protein Size and Purity

The absorbance at 280 nm of purified protein was measured and protein concentration calculated using the extinction coefficient and mass determined by the ProtParam tool available on the ExPASy.org website. Fc-tagged proteins expressed in *Drosophila* cells are N-glycosylated with two 982.9 Da molecules of $Man_3GlcNAc_2$ (39), and so this was included in the mass calculation. Purified protein was filter sterilised and stored at 4° C. in aliquots. Protein samples were denatured and electrophoresed by SDS-PAGE and visualised by Coomassie staining against Precision markers (BioRad).

Analytical Gel Filtration (FPLC)

To further purify proteins and measure their native mass, FPLC was used as described previously (37). For the Fc-tagged proteins, FPLC analytical gel filtration was carried out on a Superdex 200 HR 10/30 column (Amersham Biosciences) equilibrated with 10 mM HEPES (pH 7.4), 150 mM NaCl, 3 mM EDTA and linked to an ÄKTA Purifier system (Amersham Biosciences). The column was calibrated with amylase (200 kDa), alcohol dehydrogenase (150 kDa), BSA (66 kDa), carbonic anhydrase (29 kDa), and cytochrome C (12.5 kDa). Purified protein was loaded at ~5 mg/ml. The molecular weights of the proteins were determined from a plot of the Ve/Vo vs. log(MW) of the standards, where Ve is the elution volume of the protein and Vo is the void volume. The void volume for the column was determined by the elution of blue dextran (2000 kDa).

Cell Culture

HaCaT human keratinocytes were grown in DMEM/F-12 (1:1) supplemented with 10% foetal bovine serum (FBS), 0.5 μg/ml hydrocortisone, 50 IU/ml penicillin, 5 μg/ml streptomycin and 1 mM L-glutamine. Immortalised $Igf2^{-/-}$ mouse embryonic fibroblasts (MEFs) were derived by us from E14 embryos ($Igf2^{-/-}$) using established procedures. Briefly, the embryo was washed in PBS, the head and liver were removed and the embryo disaggregated with forceps and cells were allowed to grow out to form a monolayer. These cells were immortalised using the 3T3 method (76). Cells were grown in DMEM supplemented with 10% FBS, 50 IU/ml penicillin, 5 μg/ml streptomycin and 1 mM L-glutamine. All cells were maintained at 37° C. in 5% carbon dioxide with humidity.

Western Blot Signaling Analysis 24 hours after seeding onto 6-well plates ($1 \times 10^5$ cells per well), cells were serum starved overnight prior to stimulation. IGFs and domain 11 constructs were pre-incubated as appropriate in serum-free media at room temperature for 10 min before placing on the cells for a further 10 min. After stimulation cells were washed twice with ice-cold PBS and immediately scraped into 100 μl lysis buffer (50 mM Tris-HCl, pH 7.5, 1% NP40, 1 mM EDTA, 120 mM NaCl, 40 mM β-glycerophosphate, 1 mM benzamidine, 1 mM NaF, 1 mM $Na_3VO_4$, 1 mM PMSF, 1 μg/ml leupeptin, 1 μg/ml antipain, 1 μg/ml pepstatin). Insoluble material was removed by centrifugation and proteins were separated under reducing conditions on 12% SDS-PAGE and transferred to PVDF membrane (Millipore) before detection with anti-phospho-(Ser473) PKB or anti-phospho-p44/42 MAPK (Thr202/Tyr204) antibodies following the manufacturer's instructions. Proteins were visualised using enhanced chemiluminescence (ECL) reagents. Equal protein loading was verified using an anti-α-tubulin antibody (Sigma).

$^3$H-Thymidine Incorporation Assay

Cells were seeded onto 24-well plates (HaCaT, $1 \times 10^4$ cells per well, MEFs $3 \times 10^4$ cells per well) in growth media. After 24 hours HaCaT cells were serum starved for 24 hrs and then treated with appropriate IGF and domain 11 constructs pre-incubated at room temperature in 500 μl of serum-free medium for 10 min. After a further 24 hrs 1 μCi $^3$H-thymidine/well was added and the cells incubated for 1 hour. Media was removed and cells washed twice with PBS before fixation in 500 μl 5% TCA for 20 min at 4° C. followed by extraction in 400 μl 0.1 M NaOH at 4° C. for 1 hour. MEFs were serum starved overnight before stimulation with appropriate IGF and domain 11 constructs pre-incubated in 500 μl of serum free media at room temperature for 10 min. 1 μCi $^3$H-thymidine per well was added with the IGFs and cells incubated for 24 hrs before fixation in 5% TCA and extraction with 0.1 M NaOH. Incorporation of $^3$H-thymidine was analysed by scintillation counting.

Statistical Analysis

Data were analysed with the student's t-test (MINITAB version 14 software, Minitab Inc., Pennsylvania, USA).

Results

Optimisation of SPR Kinetic Analysis

A chimeric protein of IGF2R domain 11 fused to rat CD4 domains 3 and 4 and carrying a biotinylation motif was generated in an analogous fashion to the multidomain proteins used previously by Linnell et al (15). SPR analysis was conducted using a BIAcore 3000 with biotinylated CD4-11 as the immobilised ligand, captured via streptavidin to the sensor chip surface. 675RU of CD4-11 (45 kDa) was immobilised to achieve a theoretical Rmax of ~110RU. A non-chimeric biotinylated CD4 was immobilised to an upstream flow cell and used for in-line reference subtraction. Using IGF-II as the analyte, experiments were performed using duplicate analyte injections of 268, 134, 67, 33.5, 16.8, 8.4, 4.2 and 2.1 nM. The resulting sensorgram profiles indicated a complex interaction mechanism that did not fit a 1:1 langmuir model (FIG. 1a). The failure of even the highest concentration to reach equilibrium over the course of the injection and failure of curves to return to the starting baseline suggests a biphasic interaction with one component that dissociated rapidly, and another that appeared to remain bound. The experiment was repeated using a CD4-11 construct carrying an I1572T mutation as the in-line reference. This mutation had previously been identified as abolishing IGF-2 binding (13, 15) and as such should provide a suitable reference for the subtraction of any non-specific binding. However, no non-specific binding to the control surface was detected, indicating that the apparent complex interaction was not due to non-specific binding but dependent upon an intact IGF-II binding site. Repeated injections of IGF-II without either regeneration or extended IGF-II injections were able to achieve response levels in excess of the theoretical providing indication that the observed sensorgram shape was not the product of a 1:1 interaction of IGF-II and the domain 11 binding pocket. Experimental conditions were modified to minimise this effect. This included decreasing the immobilisation level (down to 20RU), blocking the remaining streptavidin binding sites with free biotin (0.5 µM) or biotinylated CD4 (30 µg/ml), blocking non-specific sites by preinjecting with bovine serum albumin (Fraction V BSA, 1 mg/ml), including BSA (1 mg/ml) as a carrier during the injections, using running buffers at either pH 7, 6, or 5 or performing the experiments at either 37° C. or 20° C. However, such conditions did not prevent the apparent concentration dependent upward shift in baseline following dissociation and, as the sensorgrams did not fit a 1:1 interaction model, it was not possible to obtain kinetic data for the interaction using this approach.

A number of alternative strategies were attempted using either IGF-II or domain 11 as the immobilised binding partner. For each experiment the ligand was immobilised to achieve a theoretical Rmax of ~100RU. We first expressed a native domain 11 protein in *E. coli*, that was then refolded and purified before amine coupling to a CM5 sensor chip. Duplicate injections of 268, 134, 67, 33.5, 17.8, 8.4, 4.2 and 2.1 nM IGF-II were performed. The sensorgram (FIG. 1b) showed that the immobilised domain 11 surface was of a very low activity providing indication that very little of the immobilised protein was functional. This result may be either due to inactivation of the protein as a result of amine coupling, or covalent bonds formed between the chip carboxy-methyl dextran and lysine residues of the domain 11 IGF-II binding site. As an alternative, a domain 11 protein (amino acids 1511-1650) with a C-terminal biotinylation motif was then expressed in *Pichia pastoris* (59). The soluble secreted protein (0.5-2 mg/L of culture supernatant) was biotinylated in the culture supernatant (BirA) and immobilised to the sensor chip surface by affinity capture of biotin to streptavidin (10-15M).

Duplicate injections of 268-2.1 nM IGF-II were performed. The resulting sensorgrams again showed the apparent complex response (FIG. 1c), providing indication that the observed effect was dependent on the interaction of immobilised domain 11 with IGF-II in the flow buffer, rather than an artefact associated with the fusion of domain 11 to CD4. With biotinylated IGF-II immobilised to the cell surface, duplicate injections of nonbiotinylated CD4-11 were then performed at 240, 120, 60, 30, 15, 7.5 and 3.8 nM. The resulting sensorgrams (FIG. 1d) also appeared to show a similar complex interaction.

Repeating the approach using immobilised biotinylated IGF-II, and purified soluble domain 11, either produced from *E. coli* or *Pichia pastoris*, as the analyte at concentrations of 4096, 2048, 1024, 512, 256, 128, 64, 32, 16 and 8 nM, the sensorgrams (FIGS. 1e and f, respectively) showed that, under these experimental conditions, the interaction conforms to a standard 1:1 model, with each curve returning to the original baseline within 2-3 minutes. Kinetic parameters were assigned by global fitting the observed sensorgrams to a 1:1 langmuir model using BIAevaluation software version 4.0.1 (Table 2). As equilibrium was achieved over the course of the injection for each concentration, the dissociation affinity constant (KD) was also calculated at steady-state binding. The interaction of IGF2 with domain 11, whether obtained from *E. coli* or *Pichia pastoris*, had similar kinetic association and dissociation rates and a KD of ~100 nM, whether determined from the kinetic constants or steady state binding (Table 2). Moreover, calculation of the stoichiometry from steady state Rmax indicated that at least 80% of the soluble domain 11 expressed in either system bound IGF-II. As yeast culture supernatant provided a simple, rapid and economic method for the production of correctly folded and soluble domain 11, this method was chosen for the expression of all further constructs. SPR analysis was also performed in all subsequent experiments with biotinylated IGF-II immobilised to a streptavidin coated chip surface and domain 11 was used as the analyte.

Generation of Site-Directed Mutants within IGF2R Domain 11

Site-directed mutagenesis of pCR-11 followed by subcloning into pPIC-HIS was used to generate mutated domain 11 constructs, with a C-terminal His6 tag, for secreted expression in *Pichia pastoris*. Selected mutagenesis of individual amino acids was used to assess their contribution to IGF-II binding (See Table 1 for sequence of mutagenic primers). Of the solvent exposed amino acid side chains identified by Brown et al (7) as being potentially involved in IGF-II binding Y1542, S1543 (AB loop), F1567, T1570, I1572 (CD loop) and S1596 (FG loop) were initially mutated to alanine (FIG. 2). The role of residues G1546, G1568, P1597 and P1599 was not initially assessed as mutation of either glycine or proline would be predicted to significantly alter the conformation of the binding site. E1544 and K1545 (AB loop) were also mutated. I1572 was also mutated to threonine as this amino acid substitution had previously been characterised as abolishing IGF-II binding, and acted as a positive control (13, 15). A glycine to arginine substitution at position 1619 (GH loop) has been identified as a common human polymorphism within domain 11 of the IGF2R (FIG. 2) (60). In order to assess the functional consequence of this polymorphism a further construct bearing the G1619R substitution was also generated.

Expression and Purification of Domain 11 Constructs in *Pichia pastoris*

Figure 3:
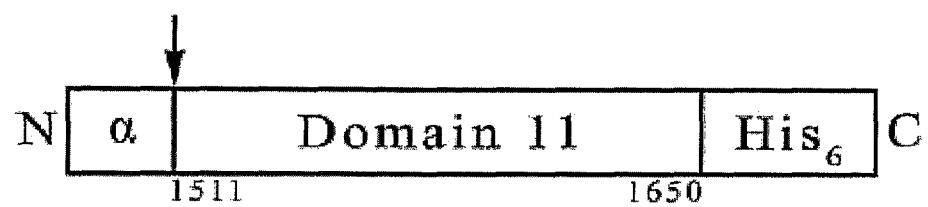

Domain 11 and the site-directed mutant forms were expressed as secreted soluble proteins in the yeast *Pichia pastoris* using the pPIC-HIS expression plasmid (FIG. 3). Following induction, analysis of each yeast supernatant by immunoblot, probed with an anti-His6 polyclonal antibody, showed the presence of the expected 17 kDa product carrying the His6 epitope tag. Coomassie staining of SDS-PAGE gels also only detected the 17 kDa product, indicating that the expressed protein was the only significant protein present in the yeast supernatants. Proteins were purified by metal chelation affinity chromatography, with typical yields of approximately 5 mg of purified protein per liter of supernatant.

Evaluation of Site-Directed IGF2R Domain 11 Mutants by SPR

Figure 4:
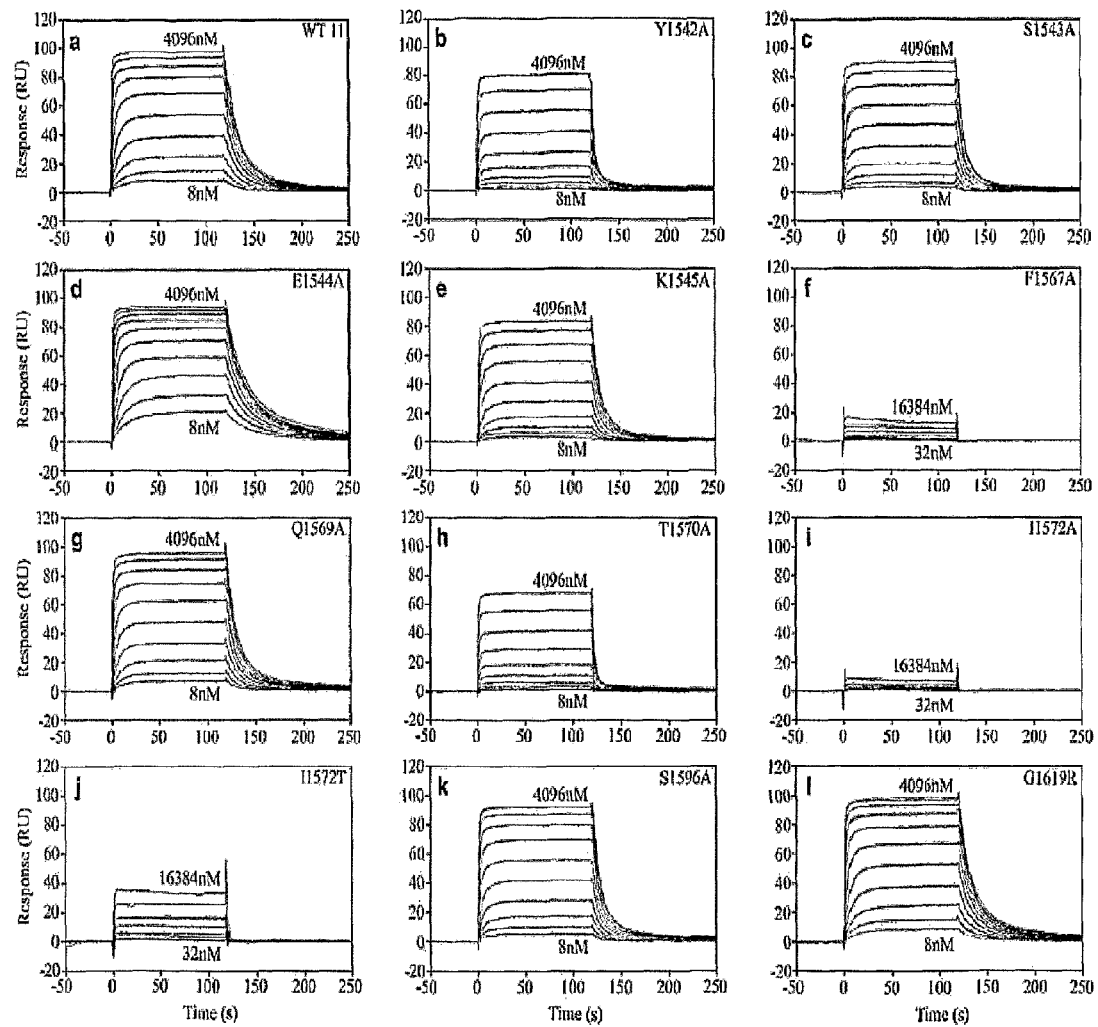

Following purification, the binding of each mutant construct to IGF2 was assessed by SPR and compared to the wild type domain 11. Sensorgrams were generated using biotinylated IGF2 immobilised to the cell surface and mutant domain 11 proteins as the free analyte (FIG. 4). For all constructs, except F1567A, I1572A and I1572T, analyte was injected in duplicate at concentrations of 4096, 2048, 1024, 512, 256, 128, 64, 32, 16 and 8 nM. A higher concentration range of 16384, 8192, 4096, 2048, 1024, 512, 256, 128, 64 and 32 nM was used for the analyte injections of F1567A, I1572A and I1572T, as pilot experiments had shown these to have a significantly reduced IGF-II affinity compared to the other mutants. As before, kinetic parameters and steady-state affinity constants were determined from the sensorgrams (Table 3).

Despite the increased analyte concentration range, neither kinetic or affinity data could be obtained for F1567A, I1572A or I1572T; the sensorgrams showed binding to be almost completely abolished for each of these mutations (FIG. 4f, and j respectively). Interestingly, the sensorgrams show an observable increase in binding to the I1572T mutant over that of I1752A, although insufficient to be accurately quantified (Table 3). Nevertheless, this confirms previous studies that have demonstrated I1572 as being essential to IGF-II binding (13, 15). Here, F1567 is identified herein as a second critical hydrophobic amino acid essential for IGF2R binding to IGF2 when mutated alone. All other mutants exhibited levels of IGF2 binding that were quantifiable by SPR, permitting assignment of kinetic parameters and steady-state affinity (Table 3). In all cases, the KD obtained from steady-state affinity analysis agreed closely with that calculated from the kinetic data. Of the remaining mutants, the T1570A mutation had the next greatest reduction in affinity (KD 900 nM) when compared to that of the wild type (KD 100 nM), placing the three residues with the greatest contribution to IGF-II binding all within the CD loop (see FIG. 2). The remaining CD loop mutation, Q1569A, caused only a minor reduction in affinity (KD=130 nM). Of the mutations within the AB loop, only Y1542A had a greater than 6 fold reduction in affinity (KD ~640 nM) compared to the wild type; S1543A and K1545A displayed a modest 2-3 fold affinity reduction (KD~260 nM and KD~290 nM respectively). The S1596A mutation situated on the FG loop also resulted in only a minor reduction in affinity (KD~170 nM). Intriguingly, the E1544A mutation on the AB loop resulted in an almost 3-fold increase in IGF-II affinity (KD~40 nM), providing indication that the acidic glutamate residue at this location is directly inhibitory to the IGF-II interaction. The IGF-II binding kinetics of the G1619R mutation, that mimics a common human polymorphism within domain 11 (60), were not significantly different to those of the wild type, providing indication that this polymorphism confers no functional consequence in terms of IGF2 binding. This might be expected from its location on the GH loop, well away from the putative IGF2 binding site. In all cases, evaluation of sensorgrams revealed that significant changes in affinity appeared to be the result of concurrent changes in both association (ka) and dissociation (kd) rate constants.

Complete bias towards modification of either 'on' or the 'off' rates was not observed. During all of the above SPR experiments, analytes were also passed over a separate flow cell on which biotinylated IGF1 had been immobilised, to assess IGF2 specificity. In all cases binding was of a very low level, insufficient to determine affinity.

SPR Analysis of Position 1544 Mutants of IGF2R Domain 11

Figure 5:
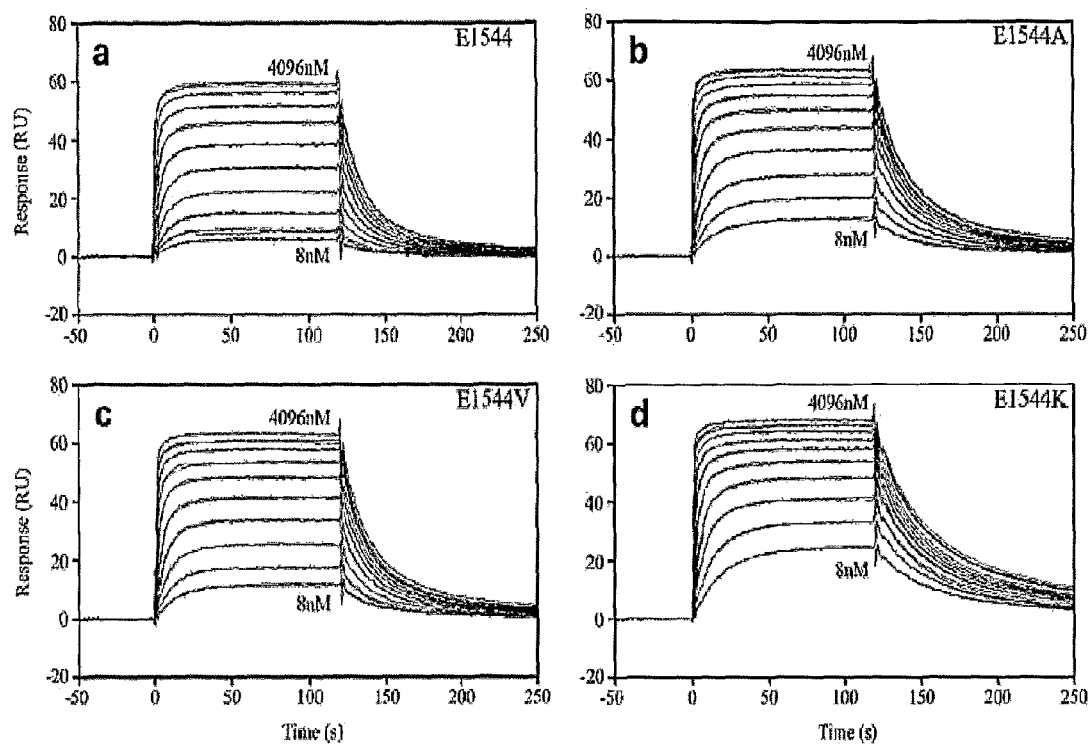

Having established that replacement of glutamate at position 1544 with alanine caused an almost 3-fold increase in IGF-II affinity, via both 'on' and 'off' rate modification, further mutations were generated at this position in order to further evaluate this observation. The acidic glutamate residue was substituted for amino acid side chains of similar size, with the hydrophobic residue valine (E1544V) and the basic residue lysine (E1544K). SPR analysis was then conducted as before, using the wild type domain 11 and the mutants E1544A, E1544V and E1544K as analyte. Again, kinetic parameters and steady-state affinity data were obtained from the resultant sensorgrams (FIG. 5 and Table 4).

Figure 7:
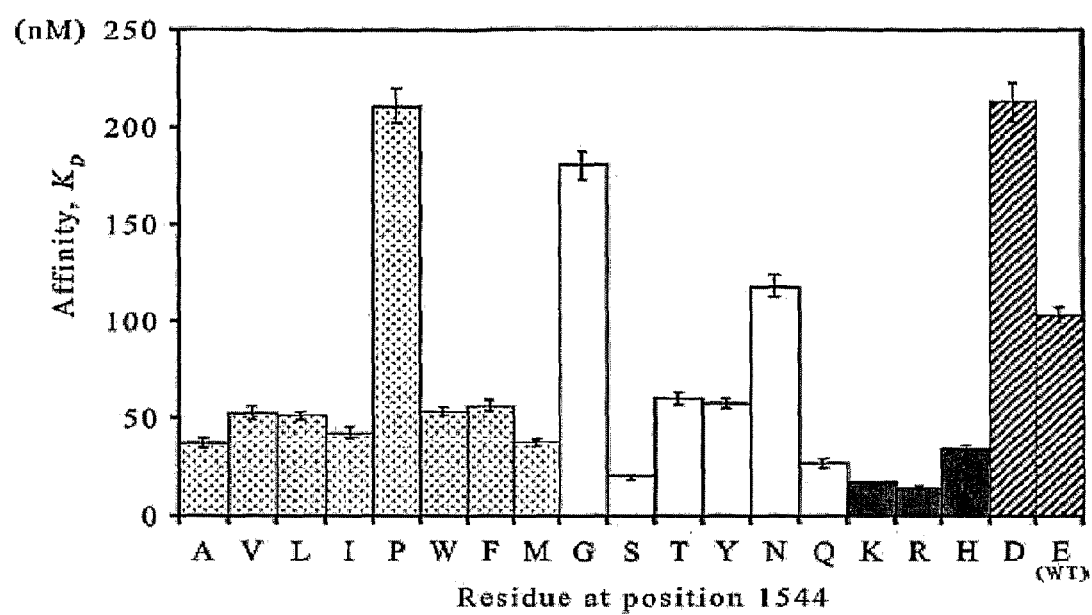

Inspection of the sensorgrams shows that the activity of the immobilised IGF-II sensor chip surface had reduced slightly with storage, with an apparent Rmax of ~60 RU. Nevertheless, ample activity remained to generate kinetic data. Like the E1544A mutant, the E1544V mutation also exhibited an, albeit slight, increase (~2-fold) in affinity over the wild type. However, the E1544K mutant displayed a ~6-fold increase in affinity (KD~15 nM) with a visibly decreased dissociation rate on sensograms (FIG. 5d), and quantified by kinetic analysis (Table 4). This data confirms our novel observation that E1544 acts as an intra-domain negative regulator of the IGF-II interaction with IGF2R domain 11, and that conversion of the acidic glutamate residue to a basic residue (E1544K) has a significant additional enhancement of affinity above that of loss of the acidic side chain (E1544A). The specificity for IGF-II is retained in E1544 mutants, with the affinity for IGF-I being still too low to be quantified. Moreover, it still shows the same apparent rank order as the IGF2 affinity, as determined by the magnitude of the response at the highest analyte concentration, in that E1544K gives the greatest response to IGF-I followed by the E1544A and E1544V mutants, with the wild type giving the least response. Site-directed mutagenesis was used to generate constructs in which E1544 was replaced with all possible amino acid residues. SPR analysis was conducted, using the purified domain 11 constructs, mutated at position 1544, as analyte. Duplicate analyte injections were performed at a concentration range of 4096-8 nM. Where possible, kinetic parameters and steady-state affinity data were obtained from the resultant sensorgrams as before (Table 5 and FIG. 7). Protein yields obtained from the mutant in which cysteine had been introduced were very poor (~1 mg/l) and sensorgrams from SPR analysis suggested a biphasic interaction that could not be easily interpreted. It seems likely that introduction of an additional cysteine residue disrupted appropriate disulphide formation, resulting in reduced yields and misfolded protein.

The inclusion of a negatively charged acidic residue at position 1544 is detrimental to affinity in this context, with both the wild type (glutamate) and aspartate conferring a relatively "poor" affinity (103.3±4.4 nM and 213.0±9.7 nM respectively). Interestingly, the aspartate residue results in a significant reduction in affinity when compared to the wild type, predominantly due to an increase in dissociation rate $(14.00±0.10×10^{-2} s^{-1}$ over $7.87±0.29×10^{-2} s^{-1})$. In each case, replacement with the amide form (glutamine and asparagine) results in an improved affinity (26.7±2.3 nM and 118.0±5.6 nM respectively), although in the case of asparagine this only resulted in an affinity close to that of the wild-type.

Of the remaining mutations all but three (P, G, N) resulted in an enhanced affinity when compared to the wild type (E). The remaining mutants displayed a relatively narrow affinity range (14.1±1.0 nM to 60.0±3.0 nM). The reduction in affinity of both proline and glycine containing mutants probably reflects a structural perturbation around the IGF-II binding site. Clearly, the greatest enhancement in affinity, above that of the wild type, was conferred by the residues lysine (16.9±0.2 nM, ~6 fold affinity increase) and arginine (14.1±1.0 nM, ~7 fold affinity increase), providing indication that the interaction of domain 11 with IGF-II can be stabilised by replacement of the negative charge at position 1544 with a positively charged residue, beyond that which is achieved by removal of the negative charge. The affinity enhancing effect of the lysine residue was confirmed by ITC (26.4±5.1 nM for E1544K). A considerable increase in affinity was also conferred by introduction of a serine residue (19.7±1.5 nM ~5 fold affinity increase), predominantly through an association rate increase ($k_a$ of 21.20±0.21×10$^5$ M$^{-1}$s$^{-1}$ compared to the wild type value of 6.62±0.13×10$^5$ M$^{-1}$ s$^{-1}$).

Validation of Biacore Affinity Data by Isothermal Titration Calorimetry

Figure 6:
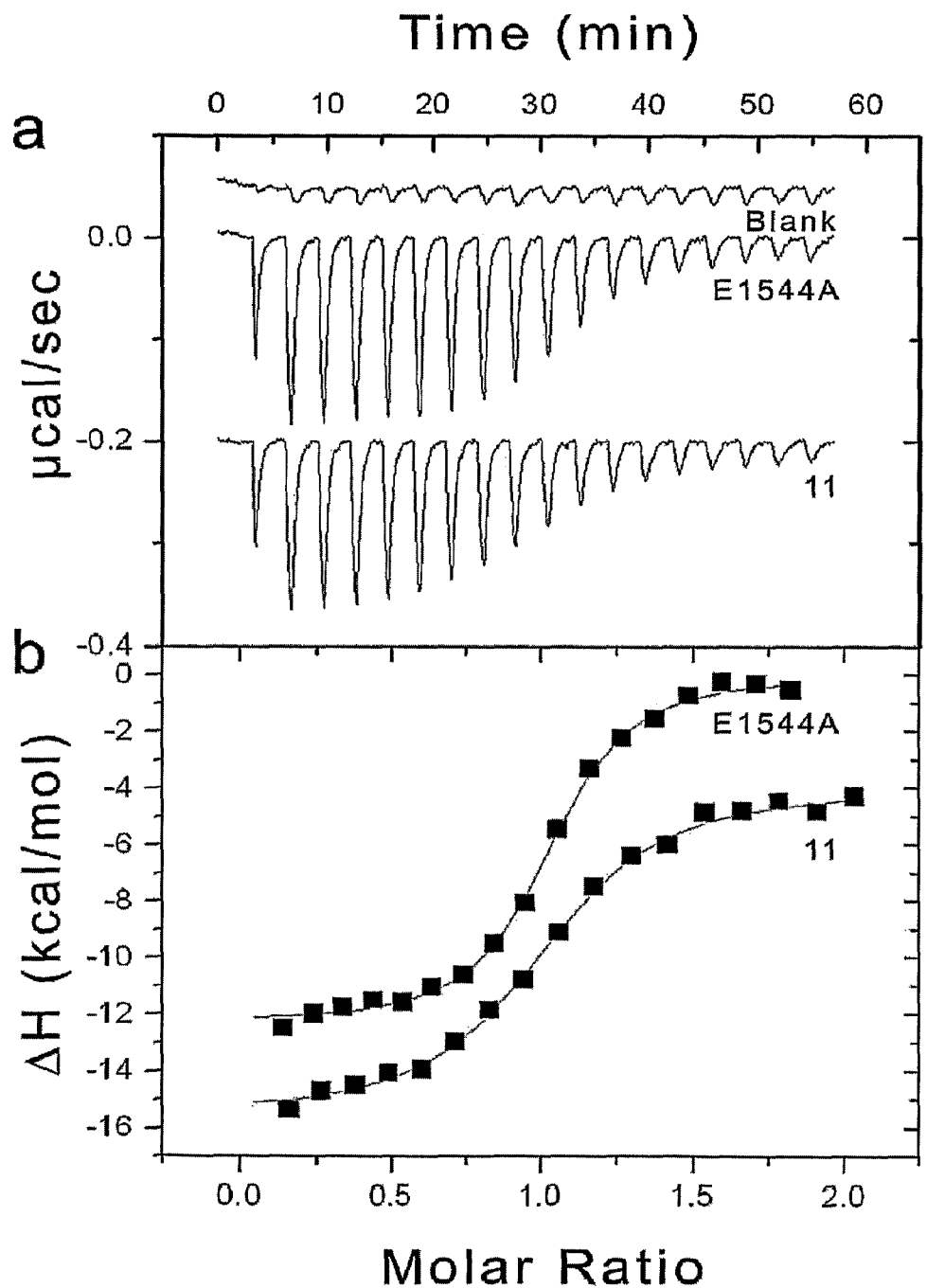

In order to validate the SPR sensorgram data, ITC was used to assess the binding affinity between domain 11 and IGF-II. The affinity of the E1544A mutant was also assessed by ITC in order to confirm whether use of a second technique agreed as to the apparent increase in affinity (FIG. 6 and Table 6). Titrations were performed using 17×15/21 injections of 40 µM IGF-II (after an initial 7.5 µl injection) into the reaction cell containing wild type domain 11 or the E1544A mutant. After subtraction of the blank titration and fitting of the integrated binding isotherms to a single site model, KD values were determined as being ~150 nM for wild-type domain 11 and ~80 nM for E1544A. These values are similar to those obtained using SPR, 103 nM and 37 nM, respectively, indicating that both independent techniques closely represent the true affinities. The two fold differences may be simply accounted for by the fidelity of both techniques. Importantly, the ITC data agrees that the E1544A mutation confers a relative affinity increase of a magnitude that is similar to that suggested by SPR (~2 fold compared to ~2.5 fold respectively).

The affinity of the wild-type domain 11 approximated to 100-150 nM when quantified using either SPR or ITC. The reproducibility and range of the sensorgram data, combined with the use of the I1572T control, indicated that the described approach would have the sensitivity to accurately quantify subtle differences in 'on' and 'off' rates induced by site directed mutations. The validated affinity of IGF-II with domain 11 alone is at least 10-100 fold less than full length IGF2R, with reported affinity constants ranging from ~2 nM (13,61) to 0.2 nM (62). Moreover, Domain 11 retains specificity for IGF-II compared to IGF-I, and the enhanced affinity of the intact receptor may be due to additional slowing of the 'off' rate by domain 13, dimerisation of the full length receptor and its affects on avidity, and additional as yet unidentified factors (6,15,56,63).

Domain 11—Fc Domain Fusions

Figure 8:
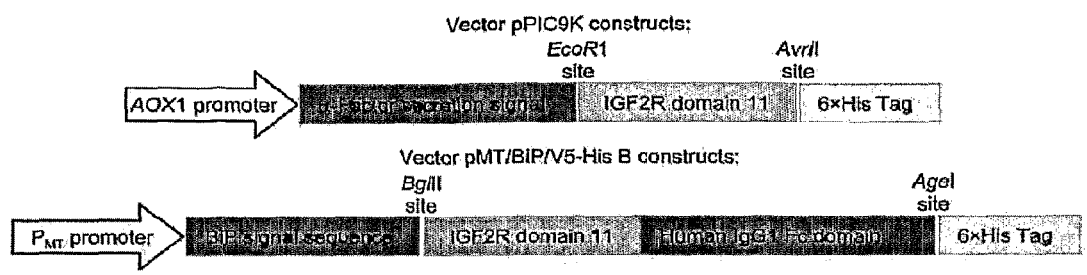
Figure 9:
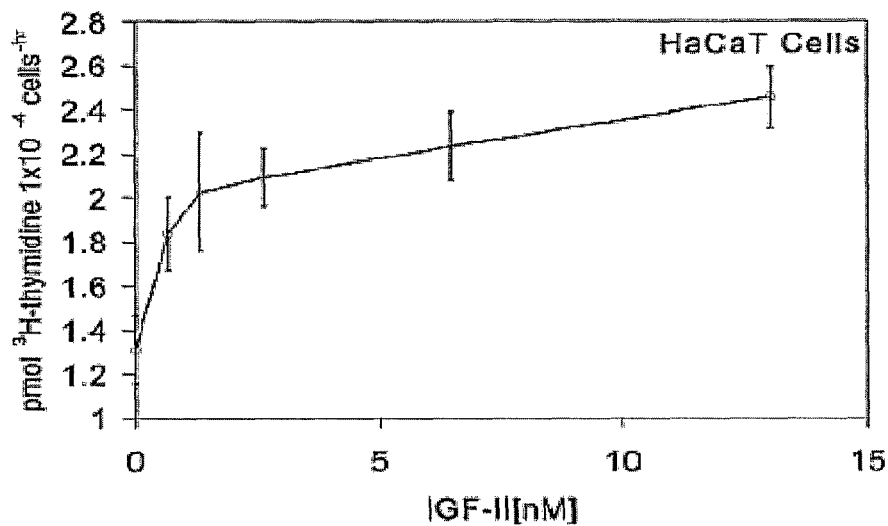
Figure 10:
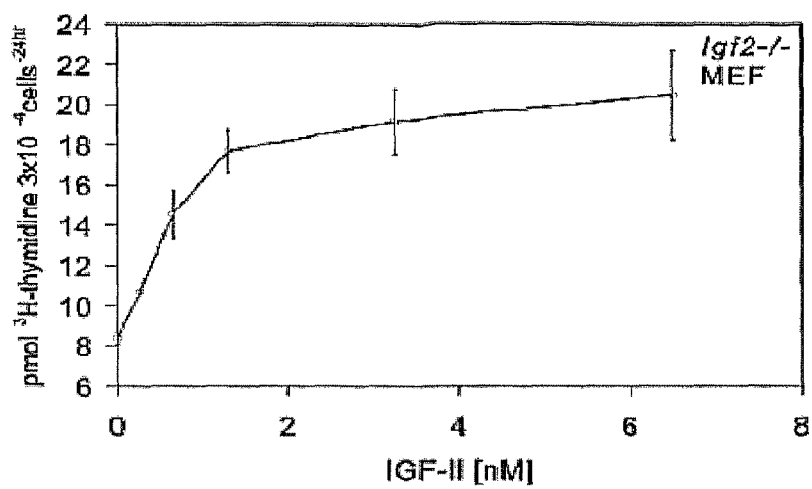

Human IgG1 Fc domain C-terminally tagged fusion proteins of the wild-type, enhanced (11$^{E1544K}$) and null (11$^{I1572A}$) mutant forms of IGF2R domain 11 (FIG. 8) were then generated. These constructs were expressed in *Drosophila* D.Mel-2 cells and secreted into the serum-free growth medium at a concentration of 10 mg per liter. A summary of the calculated physical properties of the native Fc-tagged and untagged domain 11 proteins is shown in Table 7. A denaturing coomassie brilliant blue stained gel of the purified proteins showed that proteins ran as a single band and that their denatured masses were very close to those predicted. Analytical gel filtration revealed that the native Fc-tagged domain 11 proteins were dimeric and eluted as a single peak at 13.58 ml with a mass (86 kDa), close to the predicted mass (88.06 kDa, see Table 7).

Affinity of Fc-Tagged Domain 11 Proteins for IGF-II

The affinity of versions of Fc-tagged domain 11 fusion proteins, and domain 11 constructs, for IGF-II were compared using surface plasmon resonance (BIAcore 3000). Attempts were made to immobilize Fc-tagged domain 11 proteins upon a sensor chip surface (CM5 and CM5-proteinA) but we encountered similar problems as described above with immobilised monomeric domain 11. Instead, immobilisation of biotinylated IGF-I and IGF-II on separate flow cells of a streptavidin coated sensor chip (BIAcore) generated reproducible sensorgram profiles when Fc-tagged and untagged domain 11 proteins were passed over the surface as analytes. The Fc-tagged domain 11 kinetic data performed in triplicate generated sensorgrams that were analyzed using a bivalent analyte model. Global fits of the data with a bivalent analyte model without bulk refractive index change, generated no $\chi^2$ greater than 1.94, and provided optimal fits to the data. As with the control monomeric domain 11 null mutant (11$^{I1572A}$), the 11$^{I1572A}$-Fc homodimer had no affinity for either IGF-II or IGF-I. Moreover, neither Fc-tagged wild-type domain 11 (11-Fc) nor Fc-tagged enhanced mutant domain 11 (11$^{E1544K}$-Fc), had an affinity for IGF-I, confirming that dimerisation had not altered ligand specificity. From the sensorgrams for IGF-II binding, it was apparent that 11-Fc and 11$^{E1544K}$-Fc both had high affinity for IGF-II, with Ru responses for 11$^{E1544K}$-Fc at approximately twice the amplitude of those for 11-Fc at equal concentrations. Both Fc-tagged proteins appeared to have reduced off-rates compared to the untagged monomers. A comparison of these data shows that dimerisation by Fc-tagging increased the molar affinity ($K_D$) of wild-type domain 11 for IGF-II from 118.8±3.5 nM to 3.26±0.3 nM, and the affinity of 11$^{E1544K}$ from 20.5±2.0 nM to 1.79±0.08 nM (Table 8). The 11$^{E1544K}$-Fc had the highest affinity of all the proteins tested with the molar affinity of 11$^{E1544K}$-Fc approximately twice that of 11-Fc. The improvement in affinity of the Fc-tagged dimers compared to the monomers was largely due to a substantial decrease in the off-rate ($k_d1$), from 7.87±0.29×10$^{-2}$ s$^{-1}$ to 0.445±0.04×10$^{-2}$ s$^{-1}$ for 11-Fc, and from 4.06±0.28×10$^{-2}$ s$^{-1}$ to 0.401±0.03×10$^{-2}$ s$^{-1}$ for 11$^{E1544K}$-Fc. Fc-tagging approximately doubled the on-rate ($k_a1$) for wild-type domain 11 from 6.62±0.13×10$^5$ M$^{-1}$ s$^{-1}$ to 13.65±0.01×10$^5$ M$^{-1}$s$^{-1}$, but had little effect on the on-rate for 11$^{E1544K}$, which remained high at 22.27±0.74×10$^5$ M$^{-1}$ s$^{-1}$ (Table 8). However, the substantially higher on-rate of 11$^{E1544K-}$ Fc compared to 11-Fc appeared to account for its higher molar affinity. The molar affinity of the Fc-tagged proteins was considered too high to verify by isothermal titration calorimetry (ITC) as ITC cannot be easily used to measure affinities higher than 10 nM. Minor kinetic parameters were also obtained from the sensorgram data (Table 8), but were too small to demonstrate any significant formation of the AB2 complex, where the analyte can form a bridge across two ligand molecules. This second binding event is purely a function of ligand immobilization. It is also worth noting that this is an example of a linked reaction, where the formation of the AB2 complex is entirely dependant upon the prior formation of AB, and that to dissociate, the AB2 must first decay back to AB. From the fits, the calculated $R_{max}$ for the Fc-tagged proteins was approximately 75-85% of the theoretical $R_{max}$ (286 RU) and we concluded that a high percentage of the Fc-tagged proteins were therefore functional. Increasing the valency of domain 11 was attempted following tetramerisation of biotinylated versions of domain 11 using streptavidin. This resulted in protein that could not be easily purified, and it was not possible to quantify the functional affinity (avidity).

Ability of the Domain 11 Constructs to Block Functional Activity of IGF-II In Vitro.

We next investigated the ability of the domain 11 proteins to inhibit the actions of IGF-II in vitro, by assessing the phosphorylation of downstream targets of IGF1R signaling and IGF-II induced proliferation as measured by $^3$H-thymidine incorporation into nascent DNA. We used two different cell lines, HaCaT human keratinocytes which have previously been shown to proliferate in response to IGF-II (76, 77) and immortalized Igf2$^{-/-}$ mouse embryonic fibroblasts (Igf2$^{-/-}$ MEFs) generated using a 3T3 protocol from an inbred 12952 mouse line (78). Addition of IGF-II for 10 minutes to serum-starved HaCaT cells or Igf2$^{-/-}$ MEFs led to an increase in the phosphorylation of PKB in a dose dependent manner. Stimulation of cells with increasing concentrations of IGF-II for 24 hours stimulated DNA synthesis, also in a dose dependent manner. Subsequent experiments were performed using 1.3 nM IGF-II for signaling experiments and 6.5 nM IGF-II for proliferation experiments, as these concentrations of IGF-II gave consistent maximal stimulation.

Figure 11:
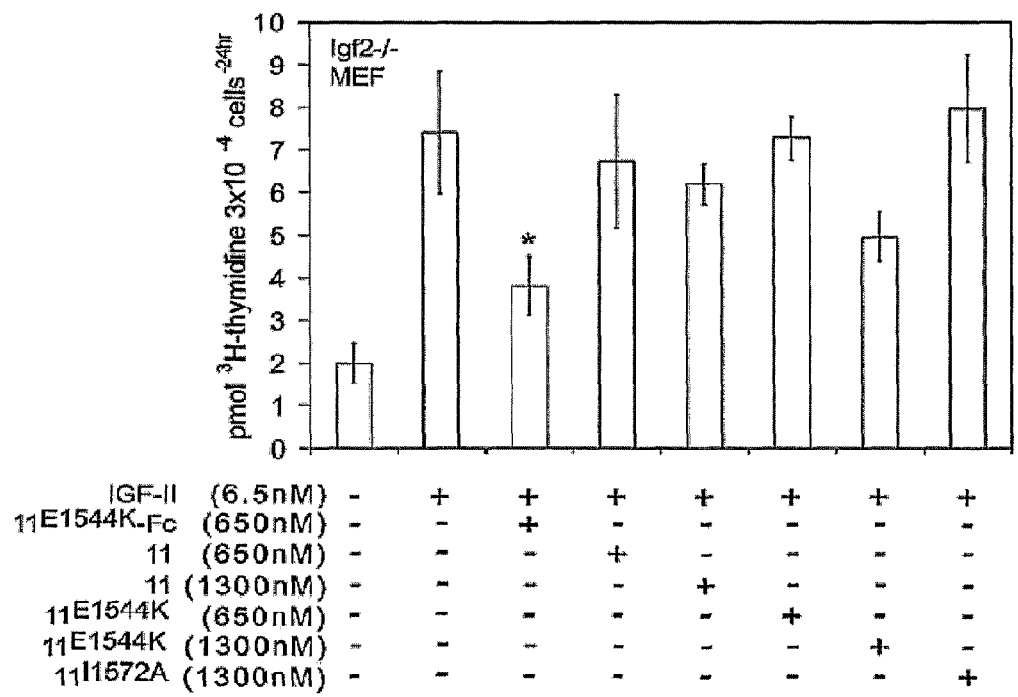
FIG. 11 shows a comparison of domain 11 constructs with two different mutations, E1544K (which enhances IGF-II binding) and I1572A (which inhibits IGF-II binding), either with or without an Fc tag, in their ability to block the actions of IGF-II in Igf2$^{-/-}$ MEFs.
Figure 12:
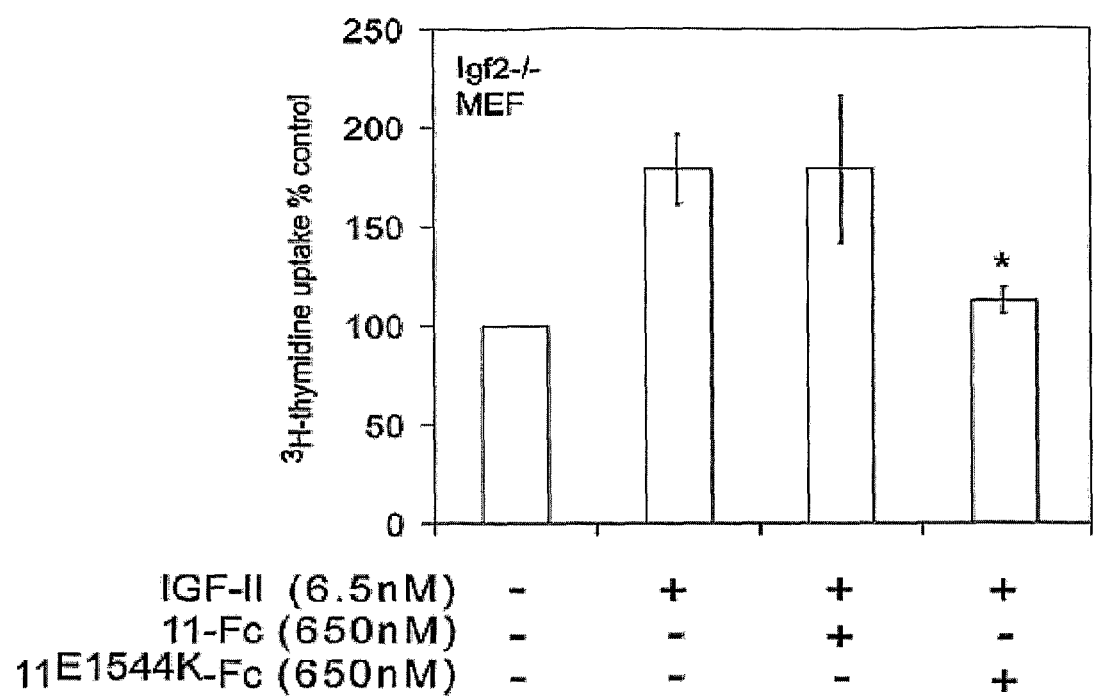
FIG. 12 shows a comparison of Fc homodimers proteins in their ability to block the actions of IGF-II in Igf2$^{-/-}$ MEFs. The 11$^{E1544K}$-Fc construct significantly inhibited IGF-II-stimulated proliferation (*p=0.024, n=3 experiments with triplicate samples, ±SEM) compared with 11-Fc even though the affinity for IGF-II is the same order of magnitude.

The domain 11 constructs $11^{wild-type}$, $11^{E1544K}$ (enhanced mutation), $11^{E1572A}$ (null mutation) 11-Fc, $11^{E1544K}$-Fc and $11^{E1572A}$-Fc were investigated for their ability to block IGF-II-stimulated proliferation and signaling in Igf2$^{-/-}$ MEFs. Of the different constructs, only the Fc tagged enhanced mutant ($11^{E1544K}$-Fc) showed significant ability to inhibit IGF-II-stimulated proliferation and activation of the IGF1R (FIGS. 11 and 12). When equivalent numbers of IGF-II binding sites were present for the single $11^{E1544K}$ domain, compared to the Fc tagged homodimer, only $11^{E1544K}$-Fc could inhibit IGF-II mediated activation of the cells significantly, even though it appears that both proliferation and signaling are slightly attenuated by $11^{E1544K}$ (FIG. 11). $11^{E1544K}$Fc was also the construct with the highest measured affinity for IGF-II (Table 8).

Figure 13:
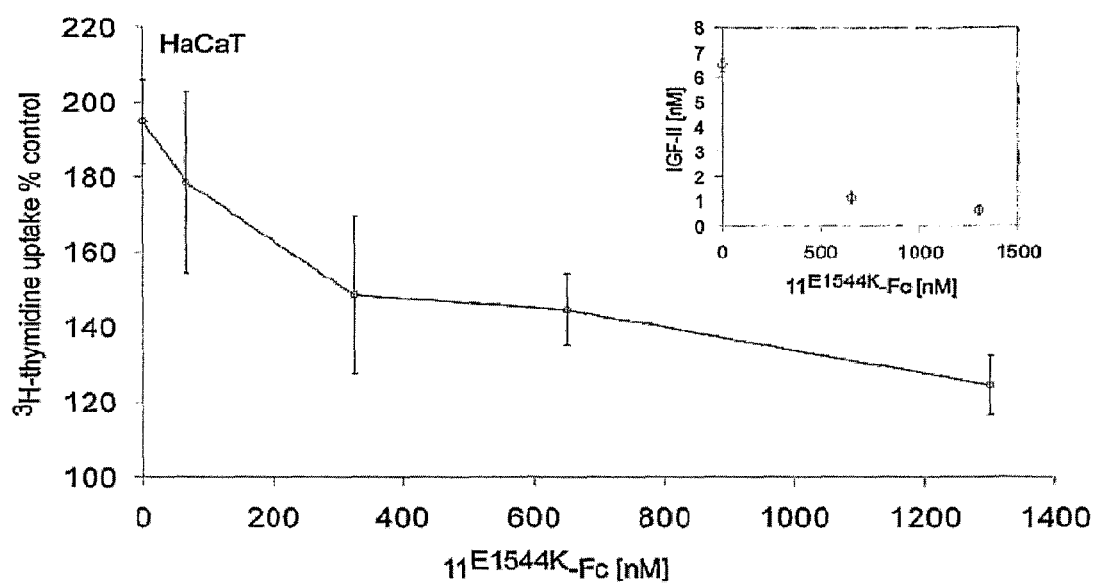
FIG. 13 shows that 11$^{E1544K}$-Fc decreases IGF-II-stimulated proliferation of HaCaT cells in a dose-dependent manner, as determined by $^3$H-thymidine incorporation.

The inhibitory properties of $11^{E1544K}$-Fc were further investigated by assessing its ability to inhibit IGF-II dependent proliferation in HaCaT cells (FIG. 13). Keeping the concentration of IGF-II constant (6.5 nM) we found that $11^{E1544K}$-Fc decreased the ability of IGF-II to stimulate proliferation in a dose dependent manner, with 650 nM and 1300 nM significantly decreasing proliferation by 50% (p=0.005) and 73% (p=0.013) respectively (FIG. 13). When the decrease in $^3$H-thymidine uptake was equated to the concentration of functional IGF-II remaining in the media, 650 nM and 1300 nM $11^{E1544K}$-Fc reduced the amount of active IGF-II by 82% and 90% respectively (see inset FIG. 13).

Figure 14:
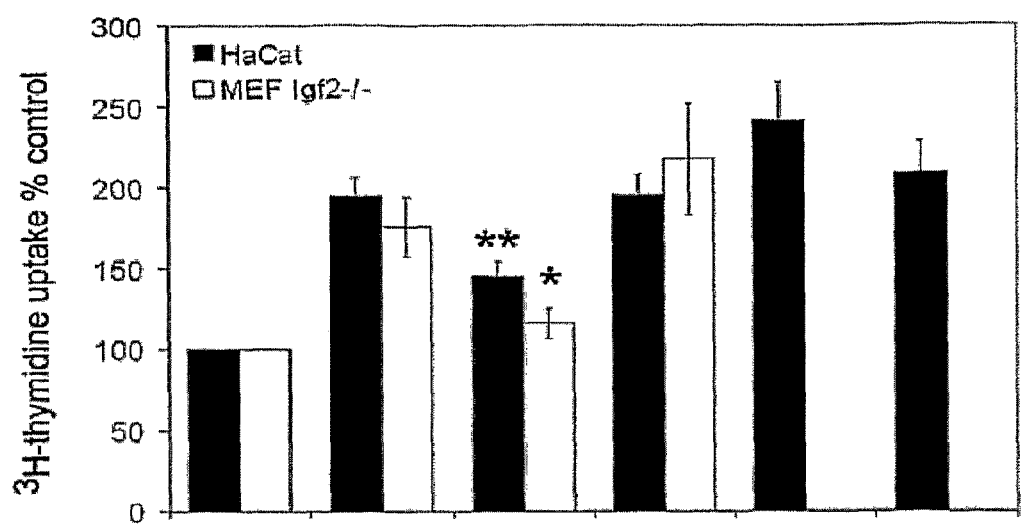
FIG. 14 shows that 11$^{E1544K}$-Fc blocks proliferation and signaling in an IGF-II dependent manner in in both HaCaT and immortalised Igf2$^{-/-}$ MEFs, as determined by 3H-thymidine incorporation.

Compared to $11^{E1544K}$-Fc, the Fc tagged null mutant ($11^{I1572A}$-Fc) that had no affinity for IGF-II, was unable to inhibit either IGF-II stimulated proliferation (FIG. 14) or stimulation of IGF1R activation as measured by phosphorylation of PKB (Akt). This provides indication that the ability of $11^{E1544K}$-Fc to inhibit the actions of IGF-II is dependent on its capacity to bind directly to the ligand. In addition, $11^{E1544K}$-Fc inhibitory function was specific for IGF-II, as it was unable to block the actions of IGF-I either on proliferation or stimulation via IGF1R.

Finally, the inhibition of chemotherapy (doxorubicin) induced apoptosis and caspase activation by IGF-II was also attenuated by $11^{I1572A}$-Fc$^a$. Overall, the surface plasmon resonance results combined with cell function assays, indicate that $11^{E1544K}$-Fc is both highly specific for IGF-II and that its inhibitory potency reflects its enhanced affinity for the IGF-II ligand.

These data present the first systematic mutational analysis of the IGF2R domain 11 binding site for IGF-II, combined with detailed and validated SPR analysis of real time binding kinetics. The previously identified CD loop mutation (I1572T), and the new mutation identified here (F1567A) appear to form the hydrophobic core of the ligand binding site. Both mutations abolish binding, and are the only two hydrophobic residues within the AB and CD loops.

For mutations of non-hydrophobic residues, SPR technology was able to quantify the relative impact of each side chain to the overall affinity. In this context, the predominant changes were detected by IGF2R domain 11 mutagenesis and IGF-II binding kinetics in the FG and AB loops, where in the latter adjacent residues were able to either enhance or reduce affinity (e.g. S1543 and E1544). Rather than a specific alteration in either the 'on' (association) or the 'off' (dissociation) rate, the interaction of IGF-II with mutated versions of domain 11 appeared to lead to relatively equal effects on both the 'on' and the 'off' rates. Most of these residues are referred to as 'second sphere', 'latch' or '0' ring residues that can substantially modify affinity in an additive fashion, and so stabilise the interaction via hydrogen bonds and salt bridges. Here, we identify a novel function for E1544 as a second sphere residue that acts as a negative regulator, with loss of the acidic side chain leading to enhanced affinity (E1544A). Further enhancement of affinity over that seen for E1544A, was established by conversion of the glutamate residue to a similar sized basic residue (E1544K). Importantly, the other residues of the AB loop failed to contribute a negative regulatory role. The AB loop residue E1544 is also conserved in mammalian species, and absent in chicken (64). As the normal function of IGF2R is to clear IGF-II via binding and internalisation, the identification of an amino acid residue that has evolved to negatively regulate this affinity is an unexpected finding.

The tumour suppressor function of IGF2R depends on its binding interaction with IGF-II, as expression of a soluble IGF2R full length receptor rescues the growth promotion consequences of biallelic expression of Igf2 in the ApcMin/+ mouse model of intestinal adenoma. Thus, the supply of soluble high affinity forms of IGF2R may be useful to target and treat the consequences of increased IGF-II in cancer. The molecules described herein may be useful in the development of high affinity therapeutic traps for IGF-II.

References

1. Dahms, N. M. et al (2002) *Biochim Biophys Acta* 1572, 317-340
2. Hassan, A. B. (2003) *Am J Pathol* 162, 3-6
3. Ghosh, P. et al (2003) *Nat Rev Mol Cell Biol* 4, 202-212
4. Oshima, A. et al (1988) *J Biol Chem* 263, 2553-2562
5. Lobel, P. et al (1988) *J Biol Chem* 263, 2563-2570
6. Olson, L. J. et al (2004) *Embo J* 23, 2019-2028
7. Brown, J. et al. (2002) *Embo J* 21, 1054-1062
8. Roberts, D. L. et al (1998) *Cell* 93, 639-648
9. Reddy, S. T. et al (2004) *J Biol Chem* 279, 38658-38667
10. Dennis, P. A. et al (1991) *Proc Natl Acad Sci USA* 88, 580-584
11. Hancock, M. K. et al (2002) *J Biol Chem* 277, 11255-11264
12. Dahms, N. M. et al (1993) *J Biol Chem* 268, 5457-5463
13. Garmroudi, F et al. (1996) *Mol Endocrinol* 10, 642-651
14. Schmidt, B. et al (1995) *J Biol Chem* 270, 14975-14982
15. Linnell, J. et al (2001) *J Biol Chem* 276, 23986-23991
16. Baker, J. et al (1993) *Cell* 75, 73-82
17. Nielsen, F. C. (1992) *Prog Growth Factor Res* 4, 257-290
18. LeRoith, D. et al. (2003) *Cancer Lett* 195, 127-137
19. Foulstone, E. et al (2005) *J Pathol* 205, 145-153

20. Oka, Y. et al (1985) *J Biol Chem* 260, 9435-9442
21. Auletta, M. et al. (1992) *J Neurosci Res* 31, 14-20
22. Grimme, S. et al (2000) *J Biol Chem* 275, 33697-33703
23. Terasawa, H. et al (1994) *Embo J* 13, 5590-5597
24. Torres, A. M. et al (1995) *J Mol Biol* 248, 385-401
25. Sakano, K. et al (1991) *J Biol Chem* 266, 20626-20635
26. Forbes, B. E. et al. (2001) *Growth Factors* 19, 163-173
27. Haig, D. et al (1991) *Cell* 64, 1045-1046 issn: 0092-8674
28. Burns, J. et al (2001) *Development* 128, 3819-3830
29. DeChiara, T. M. et al (1990) *Nature* 345, 78-80
30. Wang, Z. Q. et al (1994) *Nature* 372, 464-467
31. Lau, M. M. et al (1994) *Genes Dev* 8, 2953-2963
32. Ludwig, T. et al (1996) *Dev Biol* 177, 517-535
33. Kono, T. et al (2004) *Nature* 428, 860-864
34. Young, L. E. et al (2001) *Nat Genet.* 27, 153-154
35. Christofori, G. et al 1994) *Nature* 369, 414-418
36. Ravenel, J. D. et al. (2001) *J Natl Cancer Inst* 93, 1698-1703
37. Nosho, K. et al (2004) *Clin Cancer Res* 10, 7950-7957
38. El-Badry, O. M. et al (1990) *Cell Growth Differ* 1, 325-331
39. Zhan, S. et al (1995) *Oncogene* 11, 2503-2507
40. Douc-Rasy, S. et al (1996) *Oncogene* 12, 423-430
41. Kohda, M. et al (2001) *Mol Carcinog* 31, 184-191
42. Gelato, M. C. et al (1990) *J Clin Endocrinol Metab* 71, 1168-1174
43. Cui, H. et al (2003) *Science* 299, 1753-1755
44. Cruz-Correa, M. et al (2004) *Gastroenterology* 126, 964-970
45. De Souza, A. T. et al (1995) *Nat Genet.* 11, 447-449
46. De Souza, A. T. et al (1995) *Oncogene* 10, 1725-1729
47. Kong, F. M. et al (2000) *Oncogene* 19, 1572-1578
48. Jamieson, T. A et al (2003) *BMC Cancer* 3, 4
49. Devi, G. R. et al (1999) *Cancer Res* 59, 4314-4319
50. O'Gorman, D. B. et al (2002) *Endocrinology* 143, 4287-4294
51. Souza, R. F. et al (1999) *Oncogene* 18, 4063-4068
52. Lee, J. S. et al (2003) *Int J Cancer* 107, 564-570
53. Li, J. et al (2004) *Oncogene*
54. Uson, I. et al (2003) *Acta Crystallogr D Biol Crystallogr* 59, 57-66
55. Olson, L. J. et al. (1999) *J Biol Chem* 274, 29889-29896
56. Devi, G. R. et al (1998) *Mol Endocrinol* 12, 1661-1672
57. Myszka, D. G. (2000) *Methods Enzymol* 323, 325-340
58. Lynch, G. W. et al (1999) *Eur J Immunol* 29, 2590-2602
59. Reddy, S. T. et al. (2003) *Biochem Biophys Res Commun* 309, 643-651
60. Killian, J. K. et al (2001) *Hum Mutat* 18, 25-31
61. MacDonald, R. G. et al (1988) *Science* 239, 1134-1137
62. Tong, P. Y. et al (1988) *J Biol Chem* 263, 2585-2588
63. Kreiling, J. L. et al (2005) *J Biol Chem* 280, 21067-21077
64. Clairmont, K. B. et al (1989) *J Biol Chem* 264, 16390-16392
65. Halperin, I. et al (2004) *Structure (Camb)* 12, 1027-1038
66. Bogan, A. A., and Thorn, K. S. (1998) *J Mol Biol* 280, 1-9
67. Keskin, O. et al. (2005) *J Mol Biol* 345, 1281-1294
68. Li, X. et al (2004) *J Mol Biol* 344, 781-795
69. Li, Y. et al A. (2005) *Structure (Camb)* 13, 297-307
70. Rajamani, D. et al (2004) *Proc Natl. Acad Sci USA* 101, 11287-11292
71. Lowman, H. B. et al. (1993) *J Mol Biol* 234, 564-578
72. Lowman, H. B. et al (1991) *Biochemistry* 30 10832-10838
73. Pal, G. et al (2003) j Mol Biol 332, 195-204
74. Wu, A. M. et al (2001) *Protein Eng* 14, 1025-1033
75. Zaccheo, O. J. et al (2006) *J Mol Biol* 359, 403-421
76. Kim, H. J., and Kim, T. Y. (2004) *J Invest Dermatol* 123, 547-555
77. Barreca, A. et al (1992) *J Cell Physiol* 151, 262-268
78. DeChiara, T. M. et al (1990) *Nature* 345, 78-80
79. Scott, C. D. et al (1996) *Endocrinology* 137, 873-878
80. Scott, C. D. et al (2000) *J Cell Physiol* 182, 62-68
81. Lee, J. S. et al (2003) *Int J Cancer* 107, 564-570
82. Breuhahn, K. et al (2004) *Cancer Res* 64, 6058-6064

TABLE 1

| Oligonucleotide Name | Sequence (5' to 3') | |
|---|---|---|
| Y1542AF | CGGGATTCACAGCTGCTgcCAGCGAGAAGGGGTTGG | (SEQ ID NO: 16) |
| Y1542AR | CCAACCCCTTCTCGCTGgcAGCAGCTGTGAATCCCG | (SEQ ID NO: 17) |
| S1543AF | CGGGATTCACAGCTGCTTACgcCGAGAAGGGGTTGG | (SEQ ID NO: 18) |
| S1543AR | CCAACCCCTTCTCGgcGTAAGCAGCTGTGAATCCCG | (SEQ ID NO: 19) |
| E1544AF | CACAGCTGCTTACAGCGcGAAGGGGTTGGTTTAC | (SEQ ID NO: 20) |
| E1544AR | GTAAACCAACCCCTTCgCGCTGTAAGCAGCTGTG | (SEQ ID NO: 21) |
| K1545AF | CAGCTGCTTACAGCGAGgcGGGGTTGGTTTACATGAGC | (SEQ ID NO: 22) |
| K1545AR | GCTCATGTAAACCAACCCCgcCTCGCTGTAAGCAGCTG | (SEQ ID NO: 23) |
| F1567AF | CCTGGCGTGGGGGCCTGCgcTGGACAGACCAGGATTAGC | (SEQ ID NO: 24) |
| F1567AR | GCTAATCCTGGTCTGTCCAgcGCAGGCCCCCACGCCAGG | (SEQ ID NO: 25) |
| Q1569AF | CGTGGGGGCCTGCTTTGGAgCGACCAGGATTAGCGTGG | (SEQ ID NO: 26) |
| Q1569AR | CCACGCTAATCCTGGTCgcTCCAAAGCAGGCCCCCACG | (SEQ ID NO: 27) |
| T1570AF | GCCTGCTTTGGACAGgCCAGGATTAGCGTGGGC | (SEQ ID NO: 28) |
| T1570AR | GCCCACGCTAATCCTGGcCTGTCCAAAGCAGGC | (SEQ ID NO: 29) |
| I1572AF | GCTTTGGACAGACCAGGgcTAGCGTGGGCAAGGCC | (SEQ ID NO: 30) |
| I1572AR | GGCCTTGCCCACGCTAgcCCTGGTCTGTCCAAAGC | (SEQ ID NO: 31) |
| I1572TF | GCTTTGGACAGACCAGGAcTAGCGTGGGCAAGGCC | (SEQ ID NO: 32) |
| I1572TR | GGCCTTGCCCACGCTAgTCCTGGTCTGTCCAAAGC | (SEQ ID NO: 33) |

TABLE 1-continued

| Oligonucleotide Name | Sequence (5' to 3') | |
|---|---|---|
| S1596AF | GGTGTACAAGGATGGGgCCCCTTGTCCCTCCAAATCC | (SEQ ID NO: 34) |
| S1596AR | GGATTTGGAGGGACAAGGGGcCCCATCCTTGTACACC | (SEQ ID NO: 35) |
| G1619RF | CGTGTGCAGGCCTGAGGCcaGGCCAACCAATAGGCC | (SEQ ID NO: 36) |
| G1619RR | GGCCTATTGGTTGGCCtGGCCTCAGGCCTGCACACG | (SEQ ID NO: 37) |
| E1544VF | CACAGCTGCTTACAGCGtGAAGGGGTTGGTTTAC | (SEQ ID NO: 38) |
| E1544VR | GTAAACCAACCCCTTCaCGCTGTAAGCAGCTGTG | (SEQ ID NO: 39) |
| E1544KF | CACAGCTGCTTACAGCaAGAAGGGGTTGGTTTAC | (SEQ ID NO: 40) |
| E1544KR | GTAAACCAACCCCTTCTtGCTGTAAGCAGCTGTG | (SEQ ID NO: 41) |

TABLE 2

| Source of Domain 11 | Kinetic Parameters | | | Steady state |
|---|---|---|---|---|
| | $k_a$ ($\times 10^5$ M$^{-1}$s$^{-1}$) | $k_d$ (s$^{-1}$) | $K_D$ ($\times 10^{-9}$ M) | $K_D$ ($\times 10^{-9}$ M) |
| *E. coli* | 5.53 ± 0.25 | 0.063 ± 0.003 | 114.0 ± 5.0 | 114 ± 5.4 |
| *Pichia pastoris* | 5.25 ± 0.35 | 0.053 ± 0.002 | 101.8 ± 3.6 | 103 ± 4.4 |

TABLE 3

| Loop | Mutation | Kinetic Parameters | | | Steady state | Relative |
|---|---|---|---|---|---|---|
| | | $k_a$ ($\times 10^5$ M$^{-1}$s$^{-1}$) | $k_d$ (s$^{-1}$) | $K_D$ ($\times 10^{-9}$ M) | $K_D$ ($\times 10^{-9}$ M) | Affinity |
| | WT | 5.25 ± 0.35 | 0.053 ± 0.002 | 102 ± 4 | 103 ± 4 | 1.00 |
| AB | Y1542A | 2.65 ± 0.13 | 0.169 ± 0.008 | 639 ± 5 | 633 ± 6 | 0.16 |
| | S1543A | 3.69 ± 0.16 | 0.096 ± 0.003 | 260 ± 4 | 262 ± 3 | 0.39 |
| | E1544A | 9.34 ± 1.04 | 0.033 ± 0.002 | 36 ± 2 | 37 ± 3 | 2.79 |
| | K1545A | 2.73 ± 0.15 | 0.078 ± 0.004 | 287 ± 8 | 289 ± 10 | 0.36 |
| CD | F1567A | — | — | — | — | — |
| | Q1569A | 5.29 ± 0.19 | 0.069 ± 0.001 | 130 ± 4 | 130 ± 3 | 0.80 |
| | T1570A | 2.95 ± 0.03 | 0.281 ± 0.002 | 954 ± 8 | 930 ± 12 | 0.11 |
| | I1572A | — | — | — | — | — |
| | I1572T | — | — | — | — | — |
| FG | S1596A | 4.41 ± 0.15 | 0.079 ± 0.004 | 179 ± 2 | 170 ± 4 | 0.61 |
| GH | G1619R | 4.39 ± 0.42 | 0.050 ± 0.003 | 114 ± 5 | 114 ± 4 | 0.90 |

TABLE 4

| Mutation | Kinetic Parameters | | | Steady state | Relative |
|---|---|---|---|---|---|
| | $k_a$ ($\times 10^5$ M$^{-1}$s$^{-1}$) | $k_d$ (s$^{-1}$) | $K_D$ ($\times 10^{-9}$ M) | $K_D$ ($\times 10^{-9}$ M) | Affinity |
| WT | 5.25 ± 0.35 | 0.053 ± 0.002 | 101.8 ± 3.6 | 103.3 ± 4.4 | 1.00 |
| E1544A | 9.34 ± 1.04 | 0.033 ± 0.002 | 35.9 ± 2.3 | 37.0 ± 2.6 | 2.79 |
| E1544V | 8.37 ± 0.42 | 0.041 ± 0.001 | 49.8 ± 2.7 | 52.7 ± 3.1 | 1.96 |
| E1544K | 15.20 ± 0.15 | 0.023 ± 0.000 | 15.2 ± 0.1 | 16.9 ± 0.2 | 6.12 |

TABLE 5

| Side-chain property | Residue at position 1544 | Kinetic Parameters | | | Steady state | Relative |
|---|---|---|---|---|---|---|
| | | $k_a$ ($\times 10^5$ M$^{-1}$s$^{-1}$) | $k_d$ ($\times 10^{-2}$ s$^{-1}$) | $K_D$ ($\times 10^{-9}$ M) | $K_D$ ($\times 10^{-9}$ M) | Affinity |
| Hydrophobic | A | 12.30 ± 0.52 | 5.58 ± 0.18 | 45.5 | 37.0 ± 2.6 | 2.79 |
| | V | 11.23 ± 0.67 | 6.75 ± 0.15 | 60.5 | 52.7 ± 3.1 | 1.96 |
| | L | 10.50 ± 0.04 | 6.55 ± 0.05 | 62.4 | 51.1 ± 1.7 | 2.02 |
| | I | 13.00 ± 0.05 | 6.49 ± 0.06 | 49.9 | 42.5 ± 2.8 | 2.43 |

TABLE 5-continued

| Side-chain property | Residue at position 1544 | Kinetic Parameters $k_a$ (×10$^5$ M$^{-1}$s$^{-1}$) | $k_d$ (×10$^{-2}$s$^{-1}$) | $K_D$ (×10$^{-9}$ M) | Steady state $K_D$ (×10$^{-9}$ M) | Relative Affinity |
|---|---|---|---|---|---|---|
|  | P | 7.34 ± 0.03 | 17.20 ± 0.08 | 234.3 | 211.0 ± 8.9 | 0.49 |
|  | W | 9.36 ± 0.05 | 5.88 ± 0.05 | 62.8 | 53.2 ± 2.2 | 1.94 |
|  | F | 11.40 ± 0.08 | 7.91 ± 0.11 | 69.4 | 56.4 ± 2.6 | 1.83 |
|  | M | 12.70 ± 0.08 | 5.66 ± 0.06 | 44.6 | 37.6 ± 1.9 | 2.75 |
| Polar | G | 11.00 ± 0.09 | 21.90 ± 0.22 | 199.1 | 180.0 ± 7.3 | 0.57 |
|  | S | 21.20 ± 0.21 | 4.94 ± 0.10 | 23.3 | 19.7 ± 1.5 | 5.24 |
|  | T | 9.98 ± 0.07 | 6.92 ± 0.07 | 69.3 | 60.0 ± 3.0 | 1.72 |
|  | Y | 9.44 ± 0.03 | 6.14 ± 0.01 | 65.0 | 57.4 ± 2.5 | 1.80 |
|  | C | — | — | — | — | — |
|  | N | 8.67 ± 0.07 | 12.20 ± 0.15 | 140.7 | 118.0 ± 5.6 | 0.88 |
|  | Q | 17.60 ± 0.19 | 5.78 ± 0.12 | 32.8 | 26.7 ± 2.3 | 3.87 |
| Basic | K | 20.23 ± 2.97 | 4.06 ± 0.28 | 20.5 | 16.9 ± 0.2 | 6.12 |
|  | R | 22.90 ± 0.06 | 4.07 ± 0.04 | 17.8 | 14.1 ± 1.0 | 7.33 |
|  | H | 18.00 ± 0.16 | 6.89 ± 0.10 | 38.3 | 33.7 ± 2.3 | 3.07 |
| Acidic | D | 6.08 ± 0.03 | 14.00 ± 0.10 | 230.3 | 213.0 ± 9.7 | 0.48 |
|  | E (WT) | 6.62 ± 0.13 | 7.87 ± 0.29 | 118.8 | 103.3 ± 4.4 | 1.00 |

TABLE 6

| Domain 11 construct | Affinity, $K_D$ (×10$^{-9}$ M) Biacore | ITC |
|---|---|---|
| WT | 103.3 ± 4.4 | 149.6 ± 4.4 |
| E1544A | 37.0 ± 2.6 | 81.4 ± 9.0 |
| E1544K | 16.9 ± 0.2 | 26.4 ± 5.1 |
| Q1569A | 129.7 ± 2.7 | 208.9 ± 13.0 |
| S1596A | 170.0 ± 3.6 | 323.6 ± 42.0 |

TABLE 7

| Protein | Molecular Weight (kDa) | PI | Ext. coefficient (M$^{-1}$ cm$^{-1}$@280 mm) |
|---|---|---|---|
| 11$^{Wild\ type}$ | 16.82 | 7.76 | 13650 |
| 11$^{E1544K}$ | " | 8.45 | " |
| 11$^{I1572A}$ | 16.77 | 7.76 | " |
| 11$^{Wild\ type}$-Fc | 88.06 | 8.02 | 94420 |
| 11$^{E1544K}$ | " | 8.36 | " |
| 11$^{I1572A}$ | 87.98 | 8.02 | " |

TABLE 8

| Protein | Major Kinetic Parameters | | | Minor Kinetic Parameters | | |
|---|---|---|---|---|---|---|
|  | ka1 (×10$^5$M$^{-1s-1}$) | kd1 (×10$^{-2}$s$^{-1}$) | $K_D$ (×10$^{-9}$M) | $k_a$2 (×10$^{-3}$s$^{-1}$) | $k_a$2 (×10$^{-5}$RU$^{-1}$s$^{-1}$) | $k_d$2 (×10$^{-4}$s$^{-1}$) |
| 11$^{Wildtype}$ | 6.62 ± 0.13 | 7.87 ± 0.29 | 118.8 ± 3.5 | 2.45 ± 0.33 | — | 121 ± 7.2 |
| 11$^{E1544K}$ | 20.23 ± 2.97 | 4.06 ± 0.28 | 20.5 ± 2.0 | 3.83 ± 1.10 | — | 79 ± 28 |
| 11$^{I1572A}$ | — | — | — | — | — | — |
| 11$^{Wildtype}$-Fc | 13.65 ± 0.01 | 0.445 ± 0.04 | 3.26 ± 0.3 | — | 7.12 ± 0.19 | 2.33 ± 0.12 |
| 11$^{E1544K}$ | 22.27 ± 0.74 | 0.401 ± 0.03 | 1.79 ± 0.08 | — | 7.86 ± 0.04 | 1.26 ± 0.03 |
| 11$^{I1572A}$ | — | — | — | — | — | — |

The invention claimed is:

1. A mutant IGF-II binding domain comprising the amino acid sequence of residues 1511 to 1650 of human IGF2R with 10 or fewer of said residues mutated, wherein residue E1544 is substituted for a non-acidic residue.

2. The mutant IGF-II binding domain of claim 1, wherein the binding domain does not bind or does not substantially bind to IGF1.

3. The mutant IGF-II binding domain of claim 1, wherein the mutated residues are mutated by substitution, insertion or deletion.

4. The mutant IGF-II binding domain of claim 1, wherein residue E1544 is substituted for a basic residue.

5. The mutant IGF-II binding domain of claim 4, wherein residue E1544 is substituted for K.

6. The mutant IGF-II binding domain of claim 4, wherein residue E1544 is substituted for R.

7. The mutant IGF-II binding domain of claim 4, wherein residue E1544 is substituted for H.

8. The mutant IGF-II binding domain of claim 4, wherein residue E1544 is substituted for S.

9. The mutant IGF-II binding domain of claim 1, wherein residues F1567 and I1572 are not mutated.

10. The mutant IGF-II binding domain of claim 9, wherein residue T1570 is not mutated.

11. The mutant IGF-II binding domain of claim 1, wherein the binding domain consists of the amino acid sequence of residues 1511 to 1650 of human IGF2R with residue E1544 substituted for a non-hydrophobic residue.

12. A fusion polypeptide comprising the IGF-II binding domain of claim 1 linked to a heterologous sequence.

13. The fusion polypeptide of claim 12 wherein the heterologous sequence comprises domain 13 of human IGF2R.

14. The fusion polypeptide of claim 12 wherein the heterologous sequence comprises an immunoglobulin Fc domain.

15. The fusion polypeptide of claim 12 wherein the heterologous sequence comprises an affinity tag.

16. A fusion polypeptide comprising one or more mutant IGF-II binding domains of claim 1.

17. An isolated nucleic acid encoding the IGF-II binding domain of claim 1.

18. A vector comprising the nucleic acid of claim 17.

19. An isolated host cell comprising the vector of claim 18.

* * * * *